US006521742B2

(12) United States Patent
Yu et al.

(10) Patent No.: US 6,521,742 B2
(45) Date of Patent: *Feb. 18, 2003

(54) HUMAN ENDOKINE ALPHA

(75) Inventors: Guo-Liang Yu, Darnestown, MD (US); Jian Ni, Rockville, MD (US); Craig A. Rosen, Laytonsville, MD (US)

(73) Assignee: Human Genome Sciences, Inc., Rockville, MD (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/345,790

(22) Filed: Jul. 1, 1999

(65) Prior Publication Data

US 2002/0099198 A1 Jul. 25, 2002

Related U.S. Application Data

(62) Division of application No. 08/912,227, filed on Aug. 15, 1997, now Pat. No. 5,998,171.
(60) Provisional application No. 60/024,058, filed on Aug. 16, 1996.

(51) Int. Cl.$^7$ .................... C07K 14/52; C12N 15/62; A61K 38/19
(52) U.S. Cl. .................. 530/351; 435/69.1; 435/69.7; 530/387.3; 424/85.1
(58) Field of Search ................... 530/350, 200, 530/351, 387.3; 435/69.1, 69.7, 71.1, 71.2, 471, 325, 320.1, 252.3, 254.11; 514/2, 8, 12; 424/85.1

(56) References Cited

U.S. PATENT DOCUMENTS

| 5,288,852 A | 2/1994 | Yamada et al. ............. 530/351 |
| 5,998,171 A | 12/1999 | Yu et al. ..................... 435/69.5 |

FOREIGN PATENT DOCUMENTS

| EP | 0 212 489 | 3/1987 |
| EP | 0 218 868 | 4/1987 |
| EP | 0 288 088 | 10/1988 |
| WO | WO 96/14328 | 5/1996 |
| WO | WO 00/50620 | 8/2000 |

OTHER PUBLICATIONS

Bowie et al. Deciphering the Message in Protein Sequences: Tolerance to Amino Acid Substitutions. Science. vol. 247, pp. 1306–1310, 1990.*
Doerks et al. Protein annotation: detective work for function prediction. Trends in Genetics. Jun. 1998, vol. 14, No. 6, pp. 248–250.*
Mikayama T. Molecular cloning and functional expression of a cDNA encoding glycosylation–inhibiting factor. Proc. Natl. Acad. Sci. USA vol. 90, pp. 10056–10060, 1993.*
Voet et al. Biochemistry. 1990. John Wiley & Sons, Inc.. pp. 126–128 and 228–234.*
Aggarwal, B.B. and K. Natarajan, "Tumor necrosis factors: Developments during the last decade," *Eur. Cytokine Netw.* 7:93–124 (Apr.–Jun. 1996).
Beutler, B. et al., "Passive Immunization Against Cachectin/Tumor Necrosis Factor Protects Mice from Lethal Effect of Endotoxin," *Science* 229:869–871 (1985).
Bringman, T.S. and B.B. Aggarwal, "Monoclonal Antibodies to Human Tumor Necrosis Factors Alpha and Beta: Application for Affinity Purification, Immunoassays, and as Structural Probes," *Hybridoma* 6:489–507 (1987).
Elliott, M.J. and R.N. Maini, "Anti–cytokine therapy in rheumatoid arthritis," *Ballière's Clin. Rheum.* 9:633–652 (Nov. 1995).
Feldmann, M. et al., "TNFα Is an Effective Therapeutic Target for Rheumatoid Arthritis," *Ann. N.Y. Acad. Sci.* 766:272–278 (Nov. 1995).
Fendly, B.M. et al., "Murine Monoclonal Antibodies Defining Neutralizing Epitopes on Tumor Necrosis Factor," *Hybridoma* 6:359–370 (1987).
Gruss, H–J. and S.K. Dower, "Tumor Necrosis Factor Ligand Superfamily: Involvement in the Pathology of Malignant Lymphomas," *Blood* 85:3378–3404 (Jun. 1995).
Hinshaw, L.B. et al., "Survival of Primates in LD$_{100}$ Septic Shock Following Therapy With Antibody to Tumor Necrosis Factor (TNFα)," *Circ. Shock* 30:279–292 (1990).
Hirai, M. et al., "Production and characterization of monoclonal antibodies to human tumor necrosis factor," *J. Immunol. Methods* 96:57–62 (1987).
Kriegler, M. et al., "A Novel Form of TNF/Cachectin Is a Cell Surface Cytotoxic Transmembrane Protein: Ramifications for the Complex Physiology of TNF," *Cell* 53:45–53 (1988).
Liang, C–M. et al., "Production and Characterization of Monoclonal Antibodies Against Recombinant Human Tumor Necrosis Factor/Cachectin," *Biochem. Biophys. Res. Comm.* 137:847–854 (1986).
Mathison, J.D. et al., "Participation of Tumor Necrosis Factor in the Mediation of Gram Negative Bacterial Lipopolysaccharide–induced Injury in Rabbits," *J. Clin. Invest.* 81:1925–1937 (1988).
Meager, A. et al., "Preparation and Characterization of Monoclonal Antibodies Directed Against Antigenic Determinants of Recombinant Human Tumor Necrosis Factor (rTNF)," *Hybridoma* 6:305–311 (1987).

(List continued on next page.)

*Primary Examiner*—Prema Mertz
(74) *Attorney, Agent, or Firm*—Sterne, Kessler, Goldstein & Fox P.L.L.C.

(57) ABSTRACT

The present invention concerns a novel member of the tumor necrosis factor (TNF) family of cytokines. In particular, isolated nucleic acid molecules are provided encoding the endokine alpha protein. Endokine alpha polypeptides are also provided, as are vectors, host cells and recombinant methods for producing the same. Also provided are diagnostic and therapeutic methods concerning TNF family-related disorders.

62 Claims, 4 Drawing Sheets

OTHER PUBLICATIONS

Möller, A. et al., "Monoclonal Antibodies to Human Tumor Necrosis Factor α:In Vitro and In Vivo Application," *Cytokine 2:*162–169 (1990).

Opal, S.M. et al., "Efficacy of a Monoclonal Antibody Directed against Tumor Necrosis Factor in Protecting Neutropenic Rats from Lethal Infection with *Pseudomonas aeruginosa,*" *J. Infect. Dis. 161:*1148–1152 (1990).

Shimamoto, Y. et al., "Monoclonal antibodies against human recombinant tumor necrosis factor: prevention of endotoxic shock," *Immunol. Letters 17:*311–318 (1998).

Silva, A.T. et al., "Prophylactic and Therapeutic Effects of a Monoclonal Antibody to Tumor Necrosis Factor–α in Experimental Gram–Negative Shock," *J. Infect. Dis. 162:*421–427 (1990).

Smith, R.A. and C. Baglioni, "The Active Form of Tumor Necrosis Factor Is a Trimer," *J. Biol. Chem. 262:*6951–6954 (1987).

Tracey, K.J. et al., "Anti–cachetin/TNF monoclonal antibodies prevent septic shock during lethal bacteraemia," *Nature 330:*662–664 (1987).

Tracey, K.J. and A. Cerami, "Tumor necrosis factor: An updated review of its biology," *Crit. Care Med. 21:*S414–S422 (1993).

van der Poll, T. and S.F. Lowry, "Tumor Necrosis Factor in Sepsis: Mediator of Multiple Organ Failure or Essential Part of Host Defense?," *Shock 3:*1–12 (Jan. 1995).

Wherry, J.C. et al., "Tumor necrosis factor and the therapeutic potential of anti–tumor necrosis factor antibodies," *Crit. Care Med. 21:*S436–S440 (1993).

Database EST–STN on MASPAR search, WashU–Merck EST Project, (St. Louis, Mo, USA), No. R38487, from Hillier et al., "yf60c04.s1 *Homo sapiens* cDNA clone 3'," (May 1995).

Database EST–STN on MASPAR search, WashU–Merck EST Project, (St. Louis, MO., USA) No. R41403, from Hillier et al., "yf94c12.s1 *Homo sapiens* cDNA clone 30225 3'," (May 1995).

Database EST–STN on MASPAR search, GenBank at National Library of Medicine, No. S78214, from Miki et al., "Disruption of the APC gene by retrotransposal insertion of L1 sequence in a colon cancer," *Cancer Research 52:*643–645 (1992).

EMBL/GENBANK/DDBJ DATA BANKS, No. P41086, EMBL U02603, from Wood, "Putative Succinate Dehydrogenase 15 KD Hydrophobic Protein" (Feb. 1995).

International Search Report for Application No. PCT/US96/13282, mailed Nov., 1996.

Wiley, S.R., et al, "Identification and Characterization of a New Member of the TNF Family that Induces Apoptosis," *Immunity 3:*673–682, Cell Press (Dec. 1995).

Gurney, A.L., et al., "Identification of a new member of the tumor necrosis factor family and its receptor, a human ortholog of mouse GITR," *Curr. Biol. 9:*251–218, Elsevier Science Ltd. (1999).

Kwon, B., et al., "Identification of a Novel Activation–inducible Protein of the Tumor Necrosis Factor Receptor Superfamily and Its Ligand," *J. Biol. Chem.274:*6056–6061, American Society for Biochemistry and Molecular Biology, Inc. (1999).

Pending Non–Provisional U.S. patent application No. 10/136,511, Yu et al., filed May 2, 2002.

* cited by examiner

```
  1 GTTTTCCACAGCTCTCATTTCTCCAAAAATGTGTTTGAGCCACTTGGAAA
 51 ATATGCCTTTAAGCCATTCAAGAACTCAAGGAGCTCAGAGATCATCCTGG
     M  P  L  S  H  S  R  T  Q  G  A  Q  R  S  S  W

101 AAGCTGTGGCTCTTTTGCTCAATAGTTATGTTGCTATTTCTTTGCTCCTT
     K  L  W  L  F  C  S  I  V  M  L  L  F  L  C  S  F

151 CAGTTGGCTAATCTTTATTTTCTCCAATTAGAGACTGCTAAGGAGCCCT
     S  W  L  I  F  I  F  L  Q  L  E  T  A  K  E  P  C

201 GTATGGCTAAGTTTGGACCATTACCCTCAAAATGGCAAATGGCATCTTCT
     M  A  K  F  G  P  L  P  S  K  W  Q  M  A  S  S

251 GAACCTCCTTGCGTGAATAAGGTGTCTGACTGGAAGCTGGAGATACTTCA
     E  P  P  C  V  N  K  V  S  D  W  K  L  E  I  L  Q

301 GAATGGCTTATATTTAATTTATGGCCAAGTGGCTCCCAATGCAAACTACA
     N  G  L  Y  L  I  Y  G  Q  V  A  P  N  A  N  Y  N

351 ATGATGTAGCTCCTTTTGAGGTGCGGCTGTATAAAAACAAAGACATGATA
     D  V  A  P  F  E  V  R  L  Y  K  N  K  D  M  I

401 CAAACTCTAACAAACAAATCTAAAATCCAAAATGTAGGAGGGACTTATGA
     Q  T  L  T  N  K  S  K  I  Q  N  V  G  G  T  Y  E

451 ATTGCATGTTGGGGACACCATAGACTTGATATTCAACTCTGAGCATCAGG
     L  H  V  G  D  T  I  D  L  I  F  N  S  E  H  Q  V

501 TTCTAAAAAATAATACCTACTGGGGTATCATTTTACTAGCAAATCCCCAA
     L  K  N  N  T  Y  W  G  I  I  L  L  A  N  P  Q

551 TTCATCTCCTAGAGACTTGATTTGATCTCCTCATTCCCTTCAGCACATGT
     F  I  S
```

FIG. 1A

```
601   AGAGGTGCCAGTGGGTGGATTGGAGGGAGAAGATATTCAATTTCTAGAGT
651   TTGTCTGTCTACAAAAATCAACACAAACAGAACTCCTCTGCACGTGAATT
701   TTCATCTATCATGCCTATCTGAAAGAGACTCAGGGGAAAAGCCAAAGACT
751   TTTGGTTGGATCTGCAGAGATACTTCATTAATCCATGATAAAACAAATAT
801   GGATGACAGAGGACATGTGCTTTTCAAAGAATCTTTATCTAATTCTTGAA
851   TTCATGAGTGGAAAATGGAGTTCTATTCCCATGGAAGATTTACCTGGTA
901   TGCAAAAGGATCTGGGGCAGTAGCCTGGCTTTGTTCTCATATTCTTGGG
951   CTGCTGTAATTCATTCTTCTCATACTCCCATCTTCTGAGACCCTCCCAAT
1001  AAAAAGTAGACTGATAGGATGGCCACAGATATGCCTACCATACCCTACTT
1051  TAGATATGGTGGTGTTAGAAGATAAAGAACAATCTGAGAACTATTGGAAT
1101  AGAGGTACAAGTGGCATAAAATGGAATGTACGCTATCTGGAAATTTCTCT
1151  TGGTTTTATCTTCCTCAGGATGCAGGGTGCTTTAAAAAGCCTTATCAAAG
1201  GAGTCATTCCGAACCCTCACGTAGAGCTTTGTGAGAACTTACTGTTGGTG
1251  TGTGTGTCTAAACATTGCTAATTGTAAAGAAAGAGTAACCATTAGTAATC
1301  ATTAGGTTTAACCCCAGAATGGTATTATCATTACTGGATTATGTCATGTA
1351  ATGATTTAGTATTTTTAGCTAGCTTTCCACAGTTTGCAAAGTGCTTTCGT
1401  AAAACAGTTAGCAATTCTATGAAGTTAATTGGGCAGGCATTTGGGGGAAA
1451  ATTTTAGTGATGAGAATGTGATAGCATAGCATAGCCAACTTTCCTCAACT
1501  CATAGGACAAGTGACTACAAGAGGCAATGGGTAGTCCCCTGCATTGCACT
1551  GTCTCAGCTTTAGAATTGTTATTTCTGCTATCGTGTTATAAGACTCTAAA
1601  ACTTAGCGAATTCACTTTTCAGGAAGCATATTCCCCTTTAGCCCAAGGTG
1651  AGCAGAGTGAAGCTACAACAGATCTTTCCTTTACCAGCACACTTTTTTTT
1701  TTTTCCTGCCTGAATCAGGGAGATCCAGGATGCTGTTCAGGCCTTATCCC
1751  AACCAAATTCCCCTCTTCACTTTGCAGGGCCCATCTTAGTCAAATGTGCT
1801  AACTTCTAAAATAATAAATAGCACTAATTCAAAAAAAAAAAAAAAAAA
```

FIG. 1B

```
  1  MS-TESMIRDVELAEEALPKKTG----------GPQGSRRCLFL-----SLFSFLIV--A  TNFalpha
  1  MT-PPERL--------FLPRVCG----------TT------LHL-----LLLGLLLVLLP  TNFbeta
  1  MPLSHSRT--------QGAQRSSWKLWLFCSIVML------LFLCSFSWLIEIFLQL--E  Endokine alpha 43  GATTLFCLLHFGVIGPQREESPRDLSLISPLAQAVRSSSRT----PSDKPVAHVVANPQA  TNFalpha
 31  GAQGL---------------PGVGLTPSAAQTARQHPKMHLAHSTLKPAAHLIGDPSK   TNFbeta
 45  TAKE------------------PCMAKFGPLP----SKWQM----ASSEP-------PCV  Endokine alpha 99  EGQLQWLNRRANALLANGVELRDNQLVVPSEGLYLIYSQVLFKGQG----CPSTHVLLTH  TNFalpha
 74  QNSLLWRANTDRAFLQDGFSLSNNSLLVPTSGIYFVYSQVVFSGKAYSPKAPSSPLYLAH  TNFbeta
 72  NKVSDWKLEILQ-----------------NGLYLIYGQV---------APNAN-----  Endokine alpha 155  TISRIAVSYQTKVNLLSAIKSPCQRETPEGAEAKPWYEPIYLGGVFQLEKGDRLSAEINR  TNFalpha
134  EVQLFSSQYPFHVPLLSSQK------MVYPGLQEPWLHSMYHGAAFQLTQGDQLSTHTDG  TNFbeta
 99  ----YNDVAPFEVRLYKNKD-----MIQTLTNKSKIQNV--GGTYELHVGDTIDLIFNS  Endokine alpha 215  PDYLDFAESGQVYFGIIAL                                          TNFalpha
188  IPHLVLS-PSTVFFGAFAL                                          TNFbeta
147  -EHQVLK-NNT-YWGIILLANPQFIS                                   Endokine alpha
```

FIG.2

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
        (A) LENGTH: 1849 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 53..559

(xi) SEQUENCE DESCRIPTION: SEQ ID NO:1:

```
GTTTTCCACA GCTCTCATTT CTCCAAAAAT GTGTTTGAGC CACTTGGAAA AT ATG          55
                                                          Met
                                                           1

CCT TTA AGC CAT TCA AGA ACT CAA GGA GCT CAG AGA TCA TCC TGG AAG       103
Pro Leu Ser His Ser Arg Thr Gln Gly Ala Gln Arg Ser Ser Trp Lys
         5                  10                  15

CTG TGG CTC TTT TGC TCA ATA GTT ATG TTG CTA TTT CTT TGC TCC TTC       151
Leu Trp Leu Phe Cys Ser Ile Val Met Leu Leu Phe Leu Cys Ser Phe
             20                  25                  30

AGT TGG CTA ATC TTT ATT TTT CTC CAA TTA GAG ACT GCT AAG GAG CCC       199
Ser Trp Leu Ile Phe Ile Phe Leu Gln Leu Glu Thr Ala Lys Glu Pro
         35                  40                  45

TGT ATG GCT AAG TTT GGA CCA TTA CCC TCA AAA TGG CAA ATG GCA TCT       247
Cys Met Ala Lys Phe Gly Pro Leu Pro Ser Lys Trp Gln Met Ala Ser
 50                  55                  60                  65

TCT GAA CCT CCT TGC GTG AAT AAG GTG TCT GAC TGG AAG CTG GAG ATA       295
```

```
Ser Glu Pro Pro Cys Val Asn Lys Val Ser Asp Trp Lys Leu Glu Ile
            70                  75                  80

CTT CAG AAT GGC TTA TAT TTA ATT TAT GGC CAA GTG GCT CCC AAT GCA         343
Leu Gln Asn Gly Leu Tyr Leu Ile Tyr Gly Gln Val Ala Pro Asn Ala
                85                  90                  95

AAC TAC AAT GAT GTA GCT CCT TTT GAG GTG CGG CTG TAT AAA AAC AAA         391
Asn Tyr Asn Asp Val Ala Pro Phe Glu Val Arg Leu Tyr Lys Asn Lys
            100                 105                 110

GAC ATG ATA CAA ACT CTA ACA AAC AAA TCT AAA ATC CAA AAT GTA GGA         439
Asp Met Ile Gln Thr Leu Thr Asn Lys Ser Lys Ile Gln Asn Val Gly
        115                 120                 125

GGG ACT TAT GAA TTG CAT GTT GGG GAC ACC ATA GAC TTG ATA TTC AAC         487
Gly Thr Tyr Glu Leu His Val Gly Asp Thr Ile Asp Leu Ile Phe Asn
130                 135                 140                 145

TCT GAG CAT CAG GTT CTA AAA AAT AAT ACC TAC TGG GGT ATC ATT TTA         535
Ser Glu His Gln Val Leu Lys Asn Asn Thr Tyr Trp Gly Ile Ile Leu
                150                 155                 160

CTA GCA AAT CCC CAA TTC ATC TCC TAGAGACTTG ATTTGATCTC CTCATTCCCT        589
Leu Ala Asn Pro Gln Phe Ile Ser
            165

TCAGCACATG TAGAGGTGCC AGTGGGTGGA TTGGAGGGAG AAGATATTCA ATTTCTAGAG       649

TTTGTCTGTC TACAAAAATC AACACAAACA GAACTCCTCT GCACGTGAAT TTTCATCTAT       709

CATGCCTATC TGAAAGAGAC TCAGGGGAAA AGCCAAAGAC TTTTGGTTGG ATCTGCAGAG       769

ATACTTCATT AATCCATGAT AAAACAAATA TGGATGACAG AGGACATGTG CTTTTCAAAG       829

AATCTTTATC TAATTCTTGA ATTCATGAGT GGAAAAATGG AGTTCTATTC CCATGGAAGA       889

TTTACCTGGT ATGCAAAAAG GATCTGGGGC AGTAGCCTGG CTTTGTTCTC ATATTCTTGG       949

GCTGCTGTAA TTCATTCTTC TCATACTCCC ATCTTCTGAG ACCCTCCCAA TAAAAAGTAG      1009

ACTGATAGGA TGGCCACAGA TATGCCTACC ATACCCTACT TTAGATATGG TGGTGTTAGA      1069

AGATAAAGAA CAATCTGAGA ACTATTGGAA TAGAGGTACA AGTGGCATAA AATGGAATGT      1129

ACGCTATCTG GAAATTCTCT TGGTTTTAT CTTCCTCAGG ATGCAGGGTG CTTTAAAAAG       1189

CCTTATCAAA GGAGTCATTC CGAACCCTCA CGTAGAGCTT TGTGAGAACT TACTGTTGGT      1249

GTGTGTGTCT AAACATTGCT AATTGTAAAG AAAGAGTAAC CATTAGTAAT CATTAGGTTT      1309

AACCCCAGAA TGGTATTATC ATTACTGGAT TATGTCATGT AATGATTTAG TATTTTTAGC      1369

TAGCTTTCCA CAGTTTGCAA AGTGCTTTCG TAAAACAGTT AGCAATTCTA TGAAGTTAAT      1429

TGGGCAGGCA TTTGGGGGAA AATTTTAGTG ATGAGAATGT GATAGCATAG CATAGCCAAC      1489

TTTCCTCAAC TCATAGGACA AGTGACTACA AGAGGCAATG GGTAGTCCCC TGCATTGCAC      1549

TGTCTCAGCT TTAGAATTGT TATTTCTGCT ATCGTGTTAT AAGACTCTAA AACTTAGCGA      1609

ATTCACTTTT CAGGAAGCAT ATTCCCCTTT AGCCCAAGGT GAGCAGAGTG AAGCTACAAC      1669

AGATCTTTCC TTTACCAGCA CACTTTTTTT TTTTTCCTGC CTGAATCAGG GAGATCCAGG     1729

ATGCTGTTCA GGCCTTATCC CAACCAAATT CCCCTCTTCA CTTTGCAGGG CCCATCTTAG     1789

TCAAATGTGC TAACTTCTAA AATAATAAAT AGCACTAATT CAAAAAAAAA AAAAAAAAA     1849

(2) INFORMATION FOR SEQ ID NO:2:

(i) SEQUENCE CHARACTERISTICS:
        (A) LENGTH: 169 amino acids
        (B) TYPE: amino acid
        (D) TOPOLOGY: linear (ii) MOLECULE TYPE: protein
```

(xi) SEQUENCE DESCRIPTION: SEQ ID NO:2:

```
Met Pro Leu Ser His Ser Arg Thr Gln Gly Ala Gln Arg Ser Ser Trp
 1               5                  10                  15

Lys Leu Trp Leu Phe Cys Ser Ile Val Met Leu Leu Phe Leu Cys Ser
            20                  25                  30

Phe Ser Trp Leu Ile Phe Ile Phe Leu Gln Leu Glu Thr Ala Lys Glu
        35                  40                  45

Pro Cys Met Ala Lys Phe Gly Pro Leu Pro Ser Lys Trp Gln Met Ala
    50                  55                  60

Ser Ser Glu Pro Pro Cys Val Asn Lys Val Ser Asp Trp Lys Leu Glu
65                  70                  75                  80

Ile Leu Gln Asn Gly Leu Tyr Leu Ile Tyr Gly Gln Val Ala Pro Asn
                85                  90                  95

Ala Asn Tyr Asn Asp Val Ala Pro Phe Glu Val Arg Leu Tyr Lys Asn
            100                 105                 110

Lys Asp Met Ile Gln Thr Leu Thr Asn Lys Ser Lys Ile Gln Asn Val
        115                 120                 125

Gly Gly Thr Tyr Glu Leu His Val Gly Asp Thr Ile Asp Leu Ile Phe
    130                 135                 140

Asn Ser Glu His Gln Val Leu Lys Asn Asn Thr Tyr Trp Gly Ile Ile
145                 150                 155                 160

Leu Leu Ala Asn Pro Gln Phe Ile Ser
                165
```

(2) INFORMATION FOR SEQ ID NO:3:

(i) SEQUENCE CHARACTERISTICS:
        (A) LENGTH: 233 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:3:

```
Met Ser Thr Glu Ser Met Ile Arg Asp Val Glu Leu Ala Glu Glu Ala
 1               5                  10                  15

Leu Pro Lys Lys Thr Gly Gly Pro Gln Gly Ser Arg Arg Cys Leu Phe
            20                  25                  30

Leu Ser Leu Phe Ser Phe Leu Ile Val Ala Gly Ala Thr Thr Leu Phe
        35                  40                  45

Cys Leu Leu His Phe Gly Val Ile Gly Pro Gln Arg Glu Glu Ser Pro
    50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
        115                 120                 125

Glu Gly Leu Tyr Leu Ile Tyr Ser Gln Val Leu Phe Lys Gly Gln Gly
    130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
```

```
                    165                 170                 175
Cys Gln Arg Glu Thr Pro Glu Gly Ala Glu Ala Lys Pro Trp Tyr Glu
                180                 185                 190

Pro Ile Tyr Leu Gly Gly Val Phe Gln Leu Glu Lys Gly Asp Arg Leu
            195                 200                 205

Ser Ala Glu Ile Asn Arg Pro Asp Tyr Leu Asp Phe Ala Glu Ser Gly
210                 215                 220

Gln Val Tyr Phe Gly Ile Ile Ala Leu
225                 230
```

(2) INFORMATION FOR SEQ ID NO:4:

(i) SEQUENCE CHARACTERISTICS:
        (A) LENGTH: 205 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:4:

```
Met Thr Pro Pro Glu Arg Leu Phe Leu Pro Arg Val Cys Gly Thr Thr
1               5                   10                  15

Leu His Leu Leu Leu Gly Leu Leu Val Leu Leu Pro Gly Ala
            20                  25                  30

Gln Gly Leu Pro Gly Val Gly Leu Thr Pro Ser Ala Ala Gln Thr Ala
            35                  40                  45

Arg Gln His Pro Lys Met His Leu Ala His Ser Thr Leu Lys Pro Ala
    50                  55                  60

Ala His Leu Ile Gly Asp Pro Ser Lys Gln Asn Ser Leu Leu Trp Arg
65                  70                  75                  80

Ala Asn Thr Asp Arg Ala Phe Leu Gln Asp Gly Phe Ser Leu Ser Asn
                85                  90                  95

Asn Ser Leu Leu Val Pro Thr Ser Gly Ile Tyr Phe Val Tyr Ser Gln
            100                 105                 110

Val Val Phe Ser Gly Lys Ala Tyr Ser Pro Lys Ala Pro Ser Ser Pro
            115                 120                 125

Leu Tyr Leu Ala His Glu Val Gln Leu Phe Ser Ser Gln Tyr Pro Phe
            130                 135                 140

His Val Pro Leu Leu Ser Ser Gln Lys Met Val Tyr Pro Gly Leu Gln
145                 150                 155                 160

Glu Pro Trp Leu His Ser Met Tyr His Gly Ala Ala Phe Gln Leu Thr
                165                 170                 175

Gln Gly Asp Gln Leu Ser Thr His Thr Asp Gly Ile Pro His Leu Val
            180                 185                 190

Leu Ser Pro Ser Thr Val Phe Phe Gly Ala Phe Ala Leu
            195                 200                 205
```

(2) INFORMATION FOR SEQ ID NO:5:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

```
GCGCCATGGC TAAGTTTGGA CCAT                                              24

(2) INFORMATION FOR SEQ ID NO:6:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

GCGAAGCTTT CAAGTCTCTA GGAGATG                                           27

(2) INFORMATION FOR SEQ ID NO:7:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

GCGGATCCCG AGACTGCTAA GGAGCC                                            26

(2) INFORMATION FOR SEQ ID NO:8:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

GCGGATCCCT AGGAGATGAA TTGGGGATTT G                                      31

(2) INFORMATION FOR SEQ ID NO:9:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

GCGGGATCCG CCATCATGCC TTTAAGCCAT TC                                     32

(2) INFORMATION FOR SEQ ID NO:10:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

GCGGATCCCT AGGAGATGAA TTGGGGATTT G                                      31
```

HUMAN ENDOKINE ALPHA

CROSS-REFERENCE TO RELATED APPLICATIONS

This application is a divisional of U.S. patent application Ser. No. 08/912,227, filed Aug. 15, 1997, now U.S. Pat. No. 5,998,171, which disclosure is herein incorporated by reference; said U.S. patent application Ser. No. 08/912,227 claims priority benefit to U.S. patent application Ser. No. 60/024,058, filed Aug. 16, 1996, which disclosure is herein incorporated by reference.

BACKGROUND OF THE INVENTION

Field of the Invention

The present invention relates to an endokine alpha protein. In particular, isolated nucleic acid molecules are provided encoding the endokine alpha protein. Endokine alpha polypeptides are also provided, as are vectors, host cells and recombinant methods for producing the same.

Related Art

The cytokine known as tumor necrosis factor-α (TNFα; also termed cachectin) is a protein secreted primarily by monocytes and macrophages in response to endotoxin or other stimuli as a soluble homotrimer of 17 kD protein subunits (Smith, R. A. et al., *J. Biol. Chem.* 262:6951–6954 (1987)). A membrane-bound 26 kD precursor form of TNF has also been described (Kriegler, M. et al., *Cell* 53:45–53 (1988)).

Accumulating evidence indicates that TNF is a regulatory cytokine with pleiotropic biological activities. These activities include: inhibition of lipoprotein lipase synthesis ("cachectin" activity) (Beutler, B. et al., *Nature* 316:552 (1985)), activation of polymorphonuclear leukocytes (Klebanoff, S. J. et al., *J. Immunol.* 136:4220 (1986); Perussia, B., et al., *J. Immunol.* 138:765 (1987)), inhibition of cell growth or stimulation of cell growth (Vilcek, J. et al., *J. Exp. Med.* 163:632 (1986); Sugarman, B. J. et al., *Science* 230:943 (1985); Lachman, L. B. et al., *J. Immunol.* 138:2913 (1987)), cytotoxic action on certain transformed cell types (Lachman, L. B. et al., supra; Darzynkiewicz, Z. et al., *Canc. Res.* 44:83 (1984)), antiviral activity (Kohase, M. et al., *Cell* 45:659 (1986); Wong, G. H. W. et al., *Nature* 323:819 (1986)), stimulation of bone resorption (Bertolini, D. R. et al., *Nature* 319:516 (1986); Saklatvala, J., *Nature* 322:547 (1986)), stimulation of collagenase and prostaglandin E2 production (Dayer, J.-M. et al., *J. Exp. Med.* 162:2163 (1985)); and immunoregulatory actions, including activation of T cells (Yokota, S. et al., *J. Immunol.* 140:531 (1988)), B cells (Kehrl, J. H. et al., *J. Exp. Med.* 166:786 (1987)), monocytes (Philip, R. et al., *Nature* 323:86 (1986)), thymocytes (Ranges, G. E. et al., *J. Exp. Med.* 167:1472 (1988)), and stimulation of the cell-surface expression of major histocompatibility complex (MHC) class I and class II molecules (Collins, T. et al., *Proc. Natl. Acad. Sci. USA* 83:446 (1986); Pujol-Borrel, R. et al., *Nature* 326:304 (1987)).

TNF is noted for its pro-inflammatory actions which result in tissue injury, such as induction of procoagulant activity on vascular endothelial cells (Pober, J. S. et al., *J. Immunol.* 136:1680 (1986)), increased adherence of neutrophils and lymphocytes (Pober, J. S. et al., *J. Immunol.* 138:3319 (1987)), and stimulation of the release of platelet activating factor from macrophages, neutrophils and vascular endothelial cells (Camussi, G. et al., *J. Exp. Med.* 166:1390 (1987)).

Recent evidence implicates TNF in the pathogenesis of many infections (Cerami, A. et al., *Immunol. Today* 9:28 (1988)), immune disorders, neoplastic pathology, e.g., in cachexia accompanying some malignancies (Oliff, A. et al., *Cell* 50:555 (1987)), and in autoimmune pathologies and graft-versus host pathology (Piguet, P.-F. et al., *J. Exp. Med.* 166:1280 (1987)). The association of TNF with cancer and infectious pathologies is often related to the host's catabolic state. A major problem in cancer patients is weight loss, usually associated with anorexia. The extensive wasting which results is known as "cachexia" (Kern, K. A. et al. *J. Parent. Enter. Nutr.* 12:286–298 (1988)). Cachexia includes progressive weight loss, anorexia, and persistent erosion of body mass in response to a malignant growth. The cachectic state is thus associated with significant morbidity and is responsible for the majority of cancer mortality. A number of studies have suggested that TNF is an important mediator of the cachexia in cancer, infectious pathology, and in other catabolic states.

TNF is thought to play a central role in the pathophysiological consequences of Gram-negative sepsis and endotoxic shock (Michie, H. R. et al., *Br. J. Surg.* 76:670–671 (1989); Debets, J. M. H. et al., *Second Vienna Shock Forum,* p.463–466 (1989); Simpson, S. Q. et al., *Crit. Care Clin.* 5:27–47 (1989)), including fever, malaise, anorexia, and cachexia. Endotoxin is a potent monocyte/macrophage activator which stimulates production and secretion of TNF (Kornbluth, S. K. et al., *J. Immunol.* 137:2585–2591 (1986)) and other cytokines. Because TNF could mimic many biological effects of endotoxin, it was concluded to be a central mediator responsible for the clinical manifestations of endotoxin-related illness. TNF and other monocyte-derived cytokines mediate the metabolic and neurohormonal responses to endotoxin Michie, H. R. et al., *N. Eng. J. Med* 318:1481–1486 (1988)). Endotoxin administration to human volunteers produces acute illness with flu-like symptoms including fever, tachycardia, increased metabolic rate and stress hormone release (Revhaug, A. et al., *Arch. Surg.* 123:162–170 (1988)). Elevated levels of circulating TNF have also been found in patients suffering from Gram-negative sepsis (Waage, A. et al., *Lancet* 1:355–357 (1987); Hammerle, A. F. et al., *Second Vienna Shock Forum* p. 715–718 (1989); Debets, J. M. H. et al., *Crit. Care Med.* 17:489–497 (1989); Calandra, T. et al., *J. Infec. Dis.* 161:982–987 (1990)).

Passive immunotherapy directed at neutralizing TNF may have a beneficial effect in Gram-negative sepsis and endotoxemia, based on the increased TNF production and elevated TNF levels in these pathology states, as discussed above.

Antibodies to a "modulator" material which was characterized as cachectin (later found to be identical to TNF) were disclosed by Cerami et al. (EPO Patent Publication 0,212, 489, Mar. 4, 1987). Such antibodies were said to be useful in diagnostic immunoassays and in therapy of shock in bacterial infections. Rubin et al. (EPO Patent Publication 0,218,868, Apr. 22, 1987) disclosed monoclonal antibodies to human TNF, the hybridomas secreting such antibodies, methods of producing such antibodies, and the use of such antibodies in immunoassay of TNF. Yone et al. (EPO Patent Publication 0,288,088, Oct. 26, 1988) disclosed anti-TNF antibodies, including mAbs, and their utility in immunoassay diagnosis of pathologies, in particular Kawasaki's pathology and bacterial infection. The body fluids of patients with Kawasaki's pathology (infantile acute febrile mucocutaneous lymph node syndrome; Kawasaki, T., *Allergy* 16:178 (1967); Kawasaki, T., *Shonica (Pediatrics)* 26:935

(1985)) were said to contain elevated TNF levels which were related to progress of the pathology (Yone et al., supra).

Other investigators have described mAbs specific for recombinant human TNF which had neutralizing activity in vitro (Liang, C-M. et al. *Biochem. Biophys. Res. Comm.* 137:847–854 (1986); Meager, A. et al., *Hybridoma* 6:305–311 (1987); Fendly et al., *Hybridoma* 6:359–369 (1987); Bringman, T. S. et al., *Hybridoma* 6:489–507 (1987); Hirai, M. et al., *J. Immunol. Meth.* 96:57–62 (1987); Moller, A. et al. (*Cytokine* 2:162–169 (1990)). Some of these mAbs were used to map epitopes of human TNF and develop enzyme immunoassays (Fendly et al., supra; Hirai et al., supra; Moller et al., supra) and to assist in the purification of recombinant TNF (Bringman et al., supra). However, these studies do not provide a basis for producing TNF neutralizing antibodies that can be used for in vivo diagnostic or therapeutic uses in humans, due to immunogenicity, lack of specificity and/or pharmaceutical suitability.

Neutralizing antisera or mAbs to TNF have been shown in mammals other than man to abrogate adverse physiological changes and prevent death after lethal challenge in experimental endotoxemia and bacteremia. This effect has been demonstrated, e.g., in rodent lethality assays and in primate pathology model systems (Mathison, J. C. et al., *J. Clin. Invest.* 81:1925–1937 (1988); Beutler, B. et al., *Science* 229:869–871 (1985); Tracey, K. J. et al., *Nature* 330:662–664 (1987); Shimamoto, Y. et al., *Immunol. Lett.* 17:311–318 (1988); Silva, A. T. et al., *J. Infect. Dis.* 162:421–427 (1990); Opal, S. M. et al., *J. Infect. Dis.* 161:1148–1152 (1990); Hinshaw, L. B. et al., *Circ. Shock* 30:279–292 (1990)).

To date, experience with anti-TNF mAb therapy in humans has been limited but shows beneficial therapeutic results, e.g., in arthritis and sepsis. See, e.g., Elliott, M. J. et al., *Baillieres Clin. Rheumatol.* 9:633–52 (1995); Feldmann M, et al., *Ann. N. Y. Acad. Sci. USA* 766:272–8 (1995); van der Poll, T. et al., *Shock* 3:1–12 (1995); Wherry et al., *Crit. Care. Med.* 21:S436–40 (1993); Tracey K. J., et al., *Crit. Care Med* 21:S415–22 (1993).

Sequence analysis of cytokine receptors has defined several subfamilies of membrane proteins (1) the Ig superfamily, (2) the hematopoietin (cytokine receptor superfamily and (3) the tumor necrosis factor (TNF)/nerve growth factor (NGF) receptor superfamily (for review of TNF superfamily see, Giruss and Dower, *Blood* 85(12) :3378–3404 (1995) and Aggarwal and Natarajan, *Eur. Cytokine Netw.*, 7(2):93–124 (1996)). The TNF/NGF receptor superfamily contains at least 10 different proteins. Gruss and Dower, supra. Ligands for these receptors have been identified and belong to at least two cytokine superfamilies. Gruss and Dower, supra.

Accordingly, there is a need to provide cytokines similar to TNF that are involved in pathological conditions. Such novel cytokines could be used to make novel antibodies or other antagonists that bind these TNF-like cytokines for therapy of TNF-like disorders.

SUMMARY OF THE INVENTION

The present invention provides isolated nucleic acid molecules comprising a polynucleotide encoding a cytokine that is similar to TNF and is believed to have similar biological effects and activities. This cytokine is named endokine alpha, and includes endokine alpha polypeptides having at least a portion of the amino acid sequence in FIG. 1A (SEQ ID NO:2) or an amino acid sequence encoded by the cDNA clone deposited as ATCC Deposit Number 97640 on Jun. 27, 1996. The nucleotide sequence, which was determined by sequencing the deposited endokine alpha cDNA clone, contains an open reading frame encoding a polypeptide of about 169 amino acid residues including an N-terminal methionine, an intracellular domain of about 17 amino acid residues, a transmembrane domain of about 26 amino acids, an extracellular domain of about 126 amino acids, and a deduced molecular weight for the complete protein of about 19 kDa.

Thus, one aspect of the invention provides an isolated nucleic acid molecule comprising a polynucleotide having a nucleotide sequence selected from the group consisting of: (a) a nucleotide sequence encoding the endokine alpha polypeptide having the complete amino acid sequence in SEQ ID NO:2; (b) a nucleotide sequence encoding the endokine alpha polypeptide having the complete amino acid sequence in SEQ ID NO:2 but minus the N-terminal methionine residue; (c) a nucleotide sequence encoding the endokine alpha polypeptide having the complete amino acid sequence encoded by the cDNA clone contained in ATCC Deposit No. 97640; and (d) a nucleotide sequence complementary to any of the nucleotide sequences in (a), (b) or (c) above.

Further embodiments of the invention include isolated nucleic acid molecules that comprise a polynucleotide having a nucleotide sequence at least 95% identical, and more preferably at least 96%, 97%, 98% or 99% identical, to any of the nucleotide sequences in (a), (b), (c), or (d), above, or a polynucleotide which hybridizes under stringent hybridization conditions to a polynucleotide in (a), (b), (c), or (d), above. This polynucleotide which hybridizes does not hybridize under stringent hybridization conditions to a polynucleotide having a nucleotide sequence consisting of only A residues or of only T residues. An additional nucleic acid embodiment of the invention relates to an isolated nucleic acid molecule comprising a polynucleotide which encodes the amino acid sequence of an epitope-bearing portion of a endokine alpha polypeptide having an amino acid sequence in (a), (b), (c), or (d), above.

The invention is further directed to nucleic acid fragments of the nucleic acid molecules described herein. Preferred nucleic acid fragments include nucleic acid molecules which encode: a polypeptide comprising the endokine alpha intracellular domain (amino acid residues from about 1 to about 17 in FIG. 1A (SEQ ID NO:2)); a polypeptide comprising the endokine alpha transmembrane domain (amino acid residues from about 18 to about 43 in FIG. 1A (SEQ ID NO:2)); and a polypeptide comprising the endokine alpha extracellular domain (amino acid residues from about 44 to about 169 in FIG. 1A (SEQ ID NO:2)).

The present invention also relates to recombinant vectors, which include the isolated nucleic acid molecules of the present invention, and to host cells containing the recombinant vectors, as well as to methods of making such vectors and host cells and for using them for production of endokine alpha polypeptides or peptides by recombinant techniques.

The invention further provides an isolated endokine alpha polypeptide having an amino acid sequence selected from the group consisting of: (a) the complete 169 amino acid sequence in SEQ ID NO:2; (b) the complete 169 amino acid sequence in SEQ ID NO:2 but minus the N-terminal methionine residue; (c) the complete amino acid sequence encoded by the cDNA clone contained in ATCC Deposit No. 97640; and (d) the amino acid sequence of an epitope-bearing portion of any one of the polypeptides of (a), (b), or (c). The polypeptides of the present invention also include polypeptides having an amino acid sequence at least 95% identical, more preferably at least 96%, 97%, 98% or 99% identical to those above.

Peptides or polypeptides having the amino acid sequence of an epitope-bearing portion of an endokine alpha polypeptide of the invention include portions of such polypeptides with at least six or seven, preferably at least nine, and more preferably at least about 30 amino acids to about 50 amino acids, although epitope-bearing polypeptides of any length up to and including the entire amino acid sequence of a polypeptide of the invention described above also are included in the invention.

In another embodiment, the invention provides an isolated antibody that binds specifically to an endokine alpha polypeptide having an amino acid sequence described in (a), (b), (c), or (d) above.

Preferred polypeptide fragments according to the present invention include a polypeptide comprising: the endokine alpha intracellular domain, the endokine alpha transmembrane domain, and the endokine alpha extracellular domain.

The invention further provides methods for isolating antibodies that bind specifically to an endokine alpha polypeptide having an amino acid sequence as described above. Such antibodies may be useful diagnostically or therapeutically as antagonists in the treatment of endokine alpha- and/or TNF-related disorders. The invention also provides a diagnostic method for determining the presence of a TNF-related disorder.

BRIEF DESCRIPTION OF THE FIGURES

FIGS. 1A–1B show the nucleotide (SEQ ID NO:1) and deduced amino acid (SEQ ID NO:2) sequences of the endokine alpha protein. Amino acids 1 to 17 represent the intracellular domain, amino acids 18 to 43 the transmembrane domain (the underlined sequence), and amino acids 44 to 169 the extracellular domain (the remaining sequence).

FIG. 2 shows the regions of similarity between the amino acid sequences of the endokine alpha protein (SEQ ID NO:2), tissue necrosis factor α (TNF-α) (SEQ ID NO:3), and TNF-β (SEQ ID NO:4). The J. Hein method was used with PAM 250 residue weight table. Shading with solid black indicates residues that match consensus exactly.

DETAILED DESCRIPTION OF THE INVENTION

Figure 3:
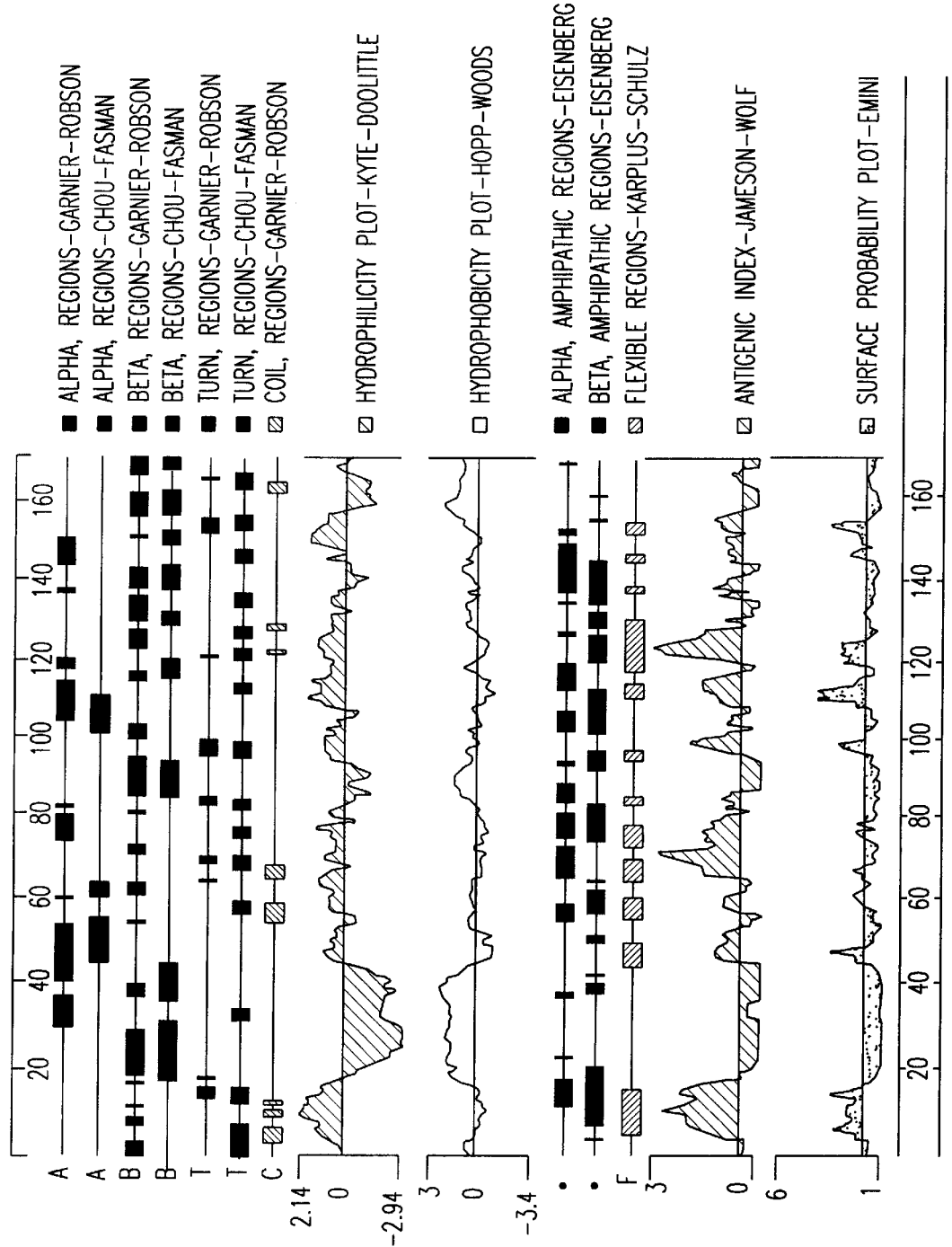
FIG. 3 provides an analysis of the endokine alpha amino acid sequence. Alpha, beta, turn and coil regions; hydrophilicity and hydrophobicity; amphipathic regions; flexible regions; antigenic index and surface probability are shown. In the "Antigenic Index—Jameson-Wolf" graph, amino acid residues 44–54, 57–68, 69–78, 94–105, 108–132 and 148–158 in FIG. 1A correspond to the shown highly antigenic regions of the endokine alpha protein.

The present invention provides isolated nucleic acid molecules comprising a polynucleotide encoding an endokine alpha protein having an amino acid sequence shown in FIG. 1A (SEQ ID NO:2), which was determined by sequencing a cloned cDNA. Endokine alpha is a novel member of the tumor necrosis factor (TNF) ligand family and shares sequence homology with human TNFα and related TNF family members (FIG. 2). The nucleotide sequence shown in FIG. 1A (SEQ ID NO: 1) was obtained by sequencing a cDNA clone, which was deposited on Jun. 27, 1996, at the American Type Culture Collection, Patent Depository, 10801 University Blvd., Manassas, Va. 20110-2209, and given accession number 97640. The deposited clone is contained in the pBluescript SK(−) plasmid (Stratagene, La Jolla, Calif.).

Nucleic Acid Molecules

Unless otherwise indicated, all nucleotide sequences determined by sequencing a DNA molecule herein were determined using an automated DNA sequencer (such as the Model 373 from Applied Biosystems, Inc.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.99% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the expected amino acid sequence encoded by a determined nucleotide sequence will be completely different from the amino acid sequence actually encoded by the sequenced DNA molecule, beginning at the point of such an insertion or deletion.

Unless otherwise indicated, each "nucleotide sequence" set forth herein is presented as a sequence of deoxyribonucleotides (abbreviated A, G, C and T). However, by "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U) where each thymidine deoxynucleotide (T) in the specified deoxynucleotide sequence in is replaced by the ribonucleotide uridine (U). For instance, reference to an RNA molecule having the sequence of FIGS. 1A–1B (SEQ ID NO:1) set forth using deoxyribonucleotide abbreviations is intended to indicate an RNA molecule having a sequence in which each deoxynucleotide A, G or C of SEQ ID NO:1 has been replaced by the corresponding ribonucleotide A, G or C, and each deoxynucleotide T has been replaced by a ribonucleotide U.

Using the information provided herein, such as the nucleotide sequence in FIGS. 1A–1B, a nucleic acid molecule of the present invention encoding an endokine alpha polypeptide can be obtained using standard cloning and screening procedures, such as those for cloning cDNAs using mRNA as starting material. Illustrative of the invention, the nucleic acid molecule described in FIGS. 1A–1B (SEQ ID NO:1) was discovered in a cDNA library derived from human brain striatum. Expressed sequence tags corresponding to a portion of the endokine alpha cDNA were also found in several endothelial libraries and a fetal liver library.

The endokine alpha gene contains an open reading frame encoding a protein of about 169 amino acid residues, an intracellular domain of about 17 amino acids (amino acid residues from about 1 to about 17 in FIGS. 1A–1B (SEQ ID NO:2)), a transmembrane domain of about 26 amino acids (amino acid residues from about 18 to about 43 in FIG. 1A (SEQ ID NO:2)), an extracellular domain of about 126 amino acids (amino acid residues from about 44 to about 169 in FIG. 1A (SEQ ID NO:2)); and a deduced molecular weight of about 19 kDa. The endokine alpha protein shown in FIG. 1A (SEQ ID NO:2) is about 30% similar and about 22% identical to human TNF-α, which can be accessed on GenBank as Accession No. U42764.

As one of ordinary skill would appreciate, due to the possibilities of sequencing errors discussed above the actual endokine alpha polypeptide encoded by the deposited cDNA comprises about 169 amino acids, but can be anywhere in the range of about 154–184 amino acids. It will also be appreciated by reasonable persons of skill in the art that, depending on the criteria used, the exact 'address' of the above-described endokine alpha protein domains may differ. Thus, for example, the exact location of the endokine alpha intracellular, transmembrane and extracellular domains shown in FIG. 1A (SEQ ID NO:2) may vary slightly (e.g., the exact address may differ by about 1 to about 5 residues compared to that shown in FIG. 1A) depending on the criteria used to define the domain.

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA can be the coding strand, also known as the sense strand, or it can be the non-coding strand, also referred to as the anti-sense strand.

By "isolated" nucleic acid molecule(s) is intended a nucleic acid molecule, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Isolated nucleic acid molecules of the present invention include DNA molecules comprising the open reading frame (ORF) shown in FIGS. 1A–1B (SEQ ID NO:1) and further include nucleic acid molecules substantially different than all or part of the ORF sequence shown in FIGS. 1A–1B (SEQ ID NO:1) but which, due to the degeneracy of the genetic code, still encode the endokine alpha protein or a fragment thereof. Of course, the genetic code is well known in the art. Thus, it would be routine for one skilled in the art to generate the degenerate variants described above.

In another aspect, the invention provides isolated nucleic acid molecules encoding the endokine alpha polypeptide having an amino acid sequence encoded by the cDNA of the clone deposited as ATCC Deposit No. 97640 on Jun. 27, 1996. The invention further provides an isolated nucleic acid molecule having the nucleotide sequence shown in FIGS. 1A–1B (SEQ ID NO:1) or the nucleotide sequence of the endokine alpha cDNA contained in the above-described deposited clone, or a nucleic acid molecule having a sequence complementary to one of the above sequences. Such isolated molecules, particularly DNA molecules, are useful as probes for gene mapping by in situ hybridization with chromosomes and for detecting expression of the endokine alpha gene in human tissue, for instance, by Northern blot analysis. As described in detail below, detecting altered endokine alpha gene expression in certain tissues or bodily fluids is indicative of certain disorders.

The present invention is further directed to fragments of the isolated nucleic acid molecules described herein. By a fragment of an isolated nucleic acid molecule having the nucleotide sequence of the deposited cDNA or the nucleotide sequence shown in FIGS. 1A–1B (SEQ ID NO. 1) is intended fragments at least about 15 nt, and more preferably at least about 20 nt, still more preferably at least about 30 nt, and even more preferably, at least about 40 nt in length which are useful as diagnostic probes and primers as discussed herein. Of course, larger fragments 50, 100, 150, 200, 250, 300, 350, 400, 450, and 500 nt in length are also useful according to the present invention as are fragments corresponding to most, if not all, of the nucleotide sequence of the deposited cDNA or as shown in FIGS. 1A–1B (SEQ ID NO. 1). By a fragment at least 20 nt in length, for example, is intended fragments which include 20 or more contiguous bases from the nucleotide sequence of the deposited cDNA or the nucleotide sequence as shown in FIG. 1A–1B (SEQ ID NO. 1). Since the gene has been deposited and the nucleotide sequence shown in FIGS. 1A–1B (SEQ ID NO 1) is provided, generating such DNA fragments would be routine to the skilled artisan. For example, restriction endonuclease cleavage or shearing by sonication could easily be used to generate fragments of various sizes. Alternatively, such fragments could be generated synthetically.

In addition, the present inventors have also identified the following related cDNA clone: HEMCG04R (SEQ ID NO:11), which, by BLAST analysis has 94% identity to nucleotides 26 to 482 of SEQ ID NO:1.

Preferred nucleic acid fragments of the present invention include nucleic acid molecules encoding: a polypeptide comprising the endokine alpha intracellular domain (amino acid residues from about 1 to about 17 in FIGS. 1A–1B (SEQ ID NO 2), or as encoded by the cDNA clone contained in ATCC Deposit No. 97640); a polypeptide comprising the endokine alpha transmembrane domain (amino acid residues from about 18 to about 43 in FIG. 1A (SEQ ID NO 2), or as encoded by the cDNA clone contained in ATCC Deposit No. 97640); and a polypeptide comprising the endokine alpha extracellular domain (amino acid residues from about 44 to about 169 in FIG. 1A (SEQ ID NO. 2), or as encoded by the cDNA clone contained in ATCC Deposit No. 97640).

Further preferred nucleic acid fragments of the present invention include nucleic acid molecules encoding epitope-bearing portions of the endokine alpha protein. In particular, such nucleic acid fragments of the present invention include nucleic acid molecules encoding: a polypeptide comprising amino acid residues from about 44 to about 158 in FIG. 1A (SEQ ID NO:2); a polypeptide comprising amino acid residues from about 44 to about 54 in FIG. 1A (SEQ ID NO:2); a polypeptide comprising amino acid residues from about 57 to about 68 in FIG. 1A (SEQ ID NO:2); a polypeptide comprising amino acid residues from about 69 to about 78 in FIG. 1 (SEQ ID NO:2); a polypeptide comprising amino acid residues from about 94 to about 105 in FIG. 1A (SEQ ID NO:2); a polypeptide comprising amino acid residues from about 108 to about 132 in FIG. 1 (SEQ ID NO:2); and a polypeptide comprising amino acid residues from about 148 to about 158 in FIG. 1 (SEQ ID NO:2). The inventors have determined that the above polypeptide fragments are antigenic regions of the endokine alpha protein. Methods for determining other such epitope-bearing portions of the endokine alpha protein are described in detail below.

In another aspect, the invention provides an isolated nucleic acid molecule comprising a polynucleotide which hybridizes under stringent hybridization conditions to a portion of the polynucleotide in a nucleic acid molecule of the invention described above, for instance, the cDNA clone contained in ATCC Deposit 97640 made on Jun. 27, 1996. By "stringent hybridization conditions" is intended overnight incubation at 42° C. in a solution comprising: 50% formamide, 5×SSC (750 mM NaCl, 75 mM trisodium citrate), 50 mM sodium phosphate (pH7.6), 5×Denhardt's solution, 10% dextran sulfate, and 20 μg/ml denatured, sheared salmon sperm DNA, followed by washing the filters in 0.1×SSC at about 65° C. By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30–70 nt of the reference polynucleotide. These are useful as diagnostic probes and primers as discussed above and in more detail below.

Of course, polynucleotides hybridizing to a larger portion of the reference polynucleotide (e.g., the deposited cDNA clone), for instance, a portion 50–500 nt in length, or even to the entire length of the reference polynucleotide, are also useful as probes according to the present invention, as are polynucleotides corresponding to most, if not all, of the nucleotide sequence of the deposited cDNA or the nucleotide sequence as shown in FIGS. 1A–1B (SEQ ID NO:1). By a portion of a polynucleotide of "at least 20 nt in length," for example, is intended 20 or more contiguous nucleotides from the nucleotide sequence of the reference polynucleotide, (e.g., the deposited cDNA or the nucleotide sequence as shown in FIGS. 1A–1B (SEQ ID NO:1)). As indicated, such portions are useful diagnostically either as a probe according to conventional DNA hybridization techniques or as primers for amplification of a target sequence by the polymerase chain reaction (PCR), as described, for instance, in Sambrook, J. et al., eds., *Molecular Cloning, A Laboratory Manual*, 2nd. edition, Cold Spring Harbor Laboratory Press, Cold Spring Harbor, N.Y. (1989), the entire disclosure of which is hereby incorporated herein by reference.

Since an endokine alpha cDNA clone has been deposited and its nucleotide sequence is provided in FIGS. 1A–1B (SEQ ID NO:1), generating polynucleotides which hybridize to a portion of the endokine alpha cDNA molecule would be routine to the skilled artisan. For example, restriction endonuclease cleavage or shearing by sonication of the endokine alpha cDNA clone could easily be used to generate DNA portions of various sizes which are polynucleotides that hybridize to a portion of the endokine alpha cDNA molecule. Alternatively, the hybridizing polynucleotides of the present invention could be generated synthetically according to known techniques.

Of course, a polynucleotide which hybridizes only to a poly A sequence (such as the 3' terminal poly(A) tract of the endokine alpha cDNA shown in FIGS. 1A–1B (SEQ ID NO:1)), or to a complementary stretch of T (or U) resides, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone).

As indicated, nucleic acid molecules of the present invention that encode an endokine alpha protein may include, but are not limited to, those encoding the amino acid sequence of the polypeptide, by itself, the coding sequence for the polypeptide and additional sequences, such as a pre-, or pro- or prepro-protein sequence; the coding sequence of the polypeptide, with or without the aforementioned additional coding sequences, together with additional, non-coding sequences, including for example, but not limited to, introns and non-coding 5' and 3' sequences, such as the transcribed, non-translated sequences that play a role in transcription, mRNA processing—including splicing and polyadenylation signals, e.g., ribosome binding and stability of mRNA; an additional coding sequence which codes for additional amino acids, such as those which provide additional functionalities. Thus, for instance, the sequence encoding the polypeptide can be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (Qiagen, Inc.), among others, many of which are publicly and/or commercially available. As described in Gentz et al., *Proc. Natl. Acad. Sci. USA* 86:821–824 (1989), for instance, hexa-histidine provides for convenient purification of the fusion protein. The "HA" tag is another peptide useful for purification which corresponds to an epitope derived from the influenza hemagglutinin (HA) protein, which has been described by Wilson et al., *Cell* 37:767 (1984). Other such fusion proteins include the endokine alpha protein fused to Fc at the N- or C-terminus.

The present invention further relates to variants of the nucleic acid molecules of the present invention, which encode portions, analogs or derivatives of the endokine alpha protein. Variants can occur naturally, such as a natural allelic variant. By an "allelic variant" is intended one of several alternate forms of a gene occupying a given locus on a chromosome of an organism. Non-naturally occurring variants can be produced, e.g., using art-known mutagenesis techniques.

Such variants include those produced by nucleotide substitutions, deletions or additions. The substitutions, deletions or additions may involve one or more nucleotides. The variants can be altered in coding or non-coding regions or both. Alterations in the coding regions can produce conservative or non-conservative amino acid substitutions, deletions or additions. Especially preferred among these are silent substitutions, additions and deletions, which do not alter the properties and activities of the endokine alpha protein or portions thereof. Also especially preferred in this regard are conservative substitutions. Most highly preferred are nucleic acid molecules encoding the endokine alpha protein having the amino acid sequence shown in FIG. 1A (SEQ ID NO:2) or the endokine alpha amino acid sequence encoded by the deposited cDNA clone.

Further embodiments of the invention include isolated nucleic acid molecules comprising a polynucleotide having a nucleotide sequence at least 90% identical, and more preferably at least 95%, 96%, 97%, 98%, or 99% identical to (a) a nucleotide sequence encoding the polypeptide having the amino acid sequence in SEQ ID NO:2; (b) a nucleotide sequence encoding the polypeptide having the amino acid sequence in SEQ ID NO:2, but lacking the N-terminal methionine; (c) a nucleotide sequence encoding the polypeptide having the amino acid sequence encoded by the cDNA clone contained in ATCC Deposit No. 97640; or (d) a nucleotide sequence complementary to any of the nucleotide sequences in (a), (b), or (c).

By a polynucleotide having a nucleotide sequence at least, for example, 95% "identical" to a reference nucleotide sequence encoding an endokine alpha polypeptide is intended that the nucleotide sequence of the polynucleotide is identical to the reference sequence except that the polynucleotide sequence may include up to five point mutations per each 100 nucleotides of the reference nucleotide sequence encoding the endokine alpha polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 95%, 96%, 97%, 98%, or 99% identical to, for instance, the nucleotide sequence shown in FIGS. 1A–1B or to the nucleotides sequence of the deposited cDNA clone can be determined conventionally using known computer programs such as the BESTFIT program (Wisconsin Sequence Analysis Package, Version 8 for Unix, Genetics Computer Group, University Research Park, 575 Science Drive, Madison, Wis. 53711). BESTFIT uses the local homology algorithm of Smith and Waterman, *Adv. Appl. Math.* 2:482–489 (1981), to find the best segment of homology between two sequences. When using BESTFIT or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

The present application is directed to such nucleic acid molecules which are at least 95%, 96%, 97%, 98%, or 99% identical to a nucleic acid sequence described above irrespective of whether they encode a polypeptide having endokine alpha protein activity. This is because, even where a particular nucleic acid molecule does not encode a polypeptide having endokine alpha activity, one of skill in the art would still know how to use the nucleic acid molecule, for instance, as a hybridization probe or a polymerase chain reaction (PCR) primer. Uses of the nucleic acid molecules of the present invention that do not encode a polypeptide having endokine alpha activity include, inter alia, (1) isolating the endokine alpha gene or allelic variants thereof from a cDNA library; (2) in situ hybridization (FISH) to metaphase chromosomal spreads to provide precise chromosomal location of the endokine alpha gene as described in Verma et al., *Human Chromosomes: a Manual of Basic Techniques,* Pergamon Press, New York (1988); and (3) Northern Blot analysis for detecting endokine alpha mRNA expression in specific tissues.

Preferred, however, are such nucleic acid molecules having sequences at least 95%, 96%, 97%, 98%, or 99% identical to a nucleic acid sequence described above which do, in fact, encode a polypeptide having endokine alpha protein activity. By "a polypeptide having endokine alpha activity" is intended polypeptides exhibiting similar, but not necessarily identical, activity as compared to the endokine alpha protein as measured in a particular biological assay. Endokine alpha activity can be assayed according to known methods. For example, a cytotoxicity assay or cell proliferation assay can be used where endokine alpha polypeptides are added to cells in culture and the effect of the endokine on the cells is determined by measuring the decrease or increase in cell numbers.

Of course, due to the degeneracy of the genetic code, one of ordinary skill in the art will immediately recognize that a large number of the nucleic acid molecules having a sequence at least 95%, 96%, 97%, 98%, or 99% identical to a nucleic acid sequence described above will encode a polypeptide "having endokine alpha protein activity." In fact, since degenerate variants all encode the same polypeptide, this will be clear to the skilled artisan even without performing the above described comparison assay. It will be further recognized in the art that, for such nucleic acid molecules that are not degenerate variants, a reasonable number will also encode a polypeptide having endokine alpha protein activity. This is because the skilled artisan is fully aware of amino acid substitutions that are either less likely or not likely to significantly effect protein function (e.g., replacing one aliphatic amino acid with a second aliphatic amino acid).

For example, guidance concerning how to make phenotypically silent amino acid substitutions is provided in Bowie, J. U. et al., *Science* 247:1306–1310 (1990), wherein the authors indicate that there are two main approaches for studying the tolerance of an amino acid sequence to change. The first method relies on the process of evolution, in which mutations are either accepted or rejected by natural selection. The second approach uses genetic engineering to introduce amino acid changes at specific positions of a cloned gene and selections or screens to identify sequences that maintain functionality. As the authors state, these studies have revealed that proteins are surprisingly tolerant of amino acid substitutions. The authors further indicate which amino acid changes are likely to be permissive at a certain position of the protein. For example, most buried amino acid residues require nonpolar side chains, whereas few features of surface side chains are generally conserved. Other such phenotypically silent substitutions are described in Bowie, J. U., et al., supra, and the references cited therein.

Vectors and Host Cells

The present invention also relates to vectors which include the isolated DNA molecules of the present invention, host cells which are genetically engineered with the recombinant vectors, and the production of endokine alpha polypeptides or portions thereof by recombinant techniques.

Recombinant constructs may be introduced into host cells using well known techniques such as infection, transduction, transfection, transvection, electroporation and transformation. The vector may be, for example, a phage, plasmid, viral or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

Preferred are vectors comprising cis-acting control regions to the polynucleotide of interest. Appropriate trans-acting factors may be supplied by the host, supplied by a complementing vector or supplied by the vector itself upon introduction into the host.

In certain preferred embodiments in this regard, the vectors provide for specific expression, which may be inducible and/or cell type-specific. Particularly preferred among such vectors are those inducible by environmental factors that are easy to manipulate, such as temperature and nutrient additives.

Expression vectors useful in the present invention include chromosomal-, episomal- and virus-derived vectors, e.g., vectors derived from bacterial plasmids, bacteriophage, yeast episomes, yeast chromosomal elements, viruses such as baculoviruses, papova viruses, vaccinia viruses, adenoviruses, fowl pox viruses, pseudorabies viruses and retroviruses, and vectors derived from combinations thereof, such as cosmids and phagemids. See, e.g., Ausubel, infra; Sambrook, infra.

The DNA insert should be operatively linked to an appropriate promoter, such as the phage lambda PL promoter, the *E. coli*: lac, trp and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the mature transcripts expressed by the constructs will include a translation initiating AUG at the beginning and a termination codon appropriately positioned at the end of the polypeptide to be translated.

As indicated, the expression vectors will preferably include at least one selectable marker. Such markers include dihydrofolate reductase or neomycin resistance for eukaryotic cell culture and tetracycline or ampicillin resistance genes for culturing in *E. coli* and other bacteria. Representative examples of appropriate hosts include bacterial cells, such as *E. coli*, Streptomyces and *Salmonella typhiniurium* cells; fungal cells, such as yeast cells; insect cells such as Drosophila S2 and Spodoptera Sf9 cells; animal cells such as CHO, COS and Bowes melanoma cells; and plant cells. Appropriate culture media and conditions for the above-described host cells are known in the art.

Among vectors preferred for use in bacteria include pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Among known bacterial promoters suitable for use in the present invention include the *E. coli* lacI and lacZ promoters, the T3 and T7 promoters, the gpt promoter, the lambda PR and PL promoters and the trp promoter. Suitable eukaryotic promoters include the CMV immediate early promoter, the HSV thymidine kinase promoter, the early and late SV40 promoters, the promoters of retroviral LTRs, such as those of the Rous sarcoma virus (RSV), and metallothionein promoters, such as the mouse metallothionein-I promoter.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., *Basic Methods in Molecular Biology* (1986).

Transcription of the DNA encoding the polypeptides of the present invention by higher eukaryotes may be increased by inserting an enhancer sequence into the vector. Enhancers are cis-acting elements of DNA, usually about from 10 to 300 bp that act to increase transcriptional activity of a promoter in a given host cell-type. Examples of enhancers include the SV40 enhancer, which is located on the late side of the replication origin at bp 100 to 270, the cytomegalovirus early promoter enhancer, the polyoma enhancer on the late side of the replication origin, and adenovirus enhancers.

For secretion of the translated protein into the lumen of the endoplasmic reticulum, into the periplasmic space or into the extracellular environment, appropriate secretion signals may be incorporated into the expressed polypeptide. The signals may be endogenous to the polypeptide or they may be heterologous signals.

The polypeptide may be expressed in a modified form, such as a fusion protein, and may include not only secretion signals but also additional heterologous functional regions. In a further example, a region of additional amino acids, particularly charged amino acids, may be added to the N-terminus of the polypeptide to improve stability and persistence in the host cell, during purification or during subsequent handling and storage. Also, as indicated, a region (s) also may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to solubilize receptors. For example, EP A 0,464,533 (also, Canadian counterpart 2,045,869) discloses fusion proteins comprising various portions of constant region of immunoglobin molecules together with another human protein or part thereof In many cases, the Fc part in the fusion protein is thoroughly advantageous for use in therapy and diagnosis and thus results, for example, in improved pharmacokinetic properties (EP A 0,232,262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as hIL5, have been fused with Fc portions for the purpose of high-throughput screening assays to identify antagonists (for example, hIL-5). See, D. Bennett et al., *Journal of Molecular Recognition* 8:52–58 (1995) and K. Johanson et al., *The Journal of Biological Chemistry* 270(16):9459–9471 (1995).

The endokine alpha protein can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

Endokine Alpha Polypeptides and Peptides

The invention further provides an isolated endokine alpha polypeptide having the amino acid sequence encoded by the deposited cDNA, or the amino acid sequence in FIGS. 1A–1B (SEQ ID NO:2), or a peptide or polypeptide comprising a portion of the above polypeptides. The terms "peptide" and "oligopeptide" are considered synonymous (as is commonly recognized) and each term can be used interchangeably as the context requires to indicate a chain of at least two amino acids coupled by peptidyl linkages. The word "polypeptide" is used herein for chains containing more than ten amino acid residues. All oligopeptide and polypeptide formulas or sequences herein are written from left to right and in the direction from amino terminus to carboxy terminus.

By "isolated" polypeptide or protein is intended a polypeptide or protein removed from its native environment. For example, recombinantly produced polypeptides and proteins expressed in recombinant host cells are considered isolated for purposes of the invention as are native or recombinant polypeptides and proteins which have been substantially purified by any suitable technique such as, for example, the one-step method described in Smith and Johnson, *Gene* 67:31–40 (1988).

It will be recognized in the art that some amino acid sequence of the endokine alpha polypeptide can be varied without significant effect of the structure or function of the protein. If such differences in sequence are contemplated, it should be remembered that there will be critical areas on the protein which determine activity. In general, it is possible to replace residues which form the tertiary structure, provided that residues performing a similar function are used. In other instances, the type of residue may be completely unimportant if the alteration occurs at a non-critical region of the protein.

Thus, the invention further includes variations of the endokine alpha polypeptide which show substantial endokine alpha polypeptide activity or which include regions of endokine alpha protein such as the protein fragments discussed below. Such mutants include deletions, insertions, inversions, repeats, and type substitutions (for example, substituting one hydrophilic residue for another, but not strongly hydrophilic for strongly hydrophobic as a rule). Small changes or such "neutral" amino acid substitutions will generally have little effect on activity.

Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

As indicated in detail above, further guidance concerning which amino acid changes are likely to be phenotypically silent (i.e., are not likely to have a significant deleterious effect on a function) can be found in Bowie, J. U., et al., "Deciphering the Message in Protein Sequences: Tolerance to Amino Acid Substitutions," *Science* 247:1306–1310 (1990).

Thus, the fragment, derivative or analog of the polypeptide of SEQ ID NO:2, or that encoded by the deposited cDNA, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as an IgG Fc fusion region peptide or leader or secretory sequence or a sequence which is employed for purification of the mature polypeptide or a proprotein sequence. Such fragments, derivatives and analogs are deemed to be within the scope of those skilled in the art from the teachings herein.

Of particular interest are substitutions of charged amino acids with another charged amino acid and with neutral or negatively charged amino acids. The latter results in proteins with reduced positive charge to improve the characteristics of the endokine alpha protein. The prevention of aggregation is highly desirable. Aggregation of proteins not only results in a loss of activity but can also be problematic when preparing pharmaceutical formulations, because they can be immunogenic. (Pinckard et al., *Clin Exp. Immunol.* 2:331–340 (1967); Robbins et al., *Diabetes* 36:838–845 (1987); Cleland et al. *Crit. Rev. Therapeutic Drug Carrier Systems* 10:307–377 (1993)).

The replacement of amino acids can also change the selectivity of binding to cell surface receptors. Ostade et al., *Nature* 361:266–268 (1993) describes certain mutations resulting in selective binding of TNF-α to only one of the two known types of TNF receptors. Thus, the endokine alpha of the present invention may include one or more amino acid substitutions, deletions or additions, either from natural mutations or human manipulation.

As indicated, changes are preferably of a minor nature, such as conservative amino acid substitutions that do not significantly affect the folding or activity of the protein (see Table 1).

TABLE 1

Conservative Amino Acid Substitutions.

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Of course, the number of amino acid substitutions a skilled artisan would make depends on many factors, including those described above. Generally speaking, the number of substitutions for any given endokine alpha polypeptide will not be more than 50, 40, 30, 20, 10, 5, or 3, depending on the objective.

Amino acids in the endokine alpha protein of the present invention that are essential for function can be identified by methods known in the art, such as site-directed mutagenesis or alanine-scanning mutagenesis (Cunningham and Wells, *Science* 244:1081–1085 (1989)). The latter procedure introduces single alanine mutations at every residue in the molecule. The resulting mutant molecules are then tested for biological activity such as receptor binding or in vitro, or in vitro proliferative activity. Sites that are critical for ligand-receptor binding can also be determined by structural analysis such as crystallization, nuclear magnetic resonance or photoaffinity labeling (Smith et al., *J. Mol. Biol.* 224:899–904 (1992) and de Vos et al. *Science* 255:306–312 (1992)).

The polypeptides of the present invention are preferably provided in an isolated form. By "isolated polypeptide" is intended a polypeptide removed from its native environment. Thus, a polypeptide produced and/or contained within a recombinant host cell is considered isolated for purposes of the present invention. Also intended as an "isolated polypeptide" are polypeptides that have been purified, partially or substantially, from a recombinant host cell. For example, a recombinantly produced version of the endokine alpha polypeptide can be substantially purified by the one-step method described in Smith and Johnson, *Gene* 67:31–40 (1988).

The polypeptides of the present invention include the polypeptides having (a) the complete amino acid sequence as shown in FIG. 1A (SEQ ID NO:2); (b) the complete amino acid sequence as shown in FIG. 1A (SEQ ID NO:2), but minus the N-terminal methionine residue; (c) the amino acid sequence of the endokine alpha polypeptide having the amino acid sequence encoded by the cDNA clone contained in ATCC Deposit No. 97640; and (d) the amino acid sequence of an epitope-bearing portion of any one of the polypeptides of (a), (b), or (c), as well as polypeptides which are at least 90% identical, more preferably at least 95%, 96%, 97%, 98% or 99% identical to a polypeptide described herein, and also include portions of such polypeptides with at least 30 amino acids and more preferably at least 50 amino acids.

By a polypeptide having an amino acid sequence at least, for example, 95% "identical" to a reference amino acid sequence of an endokine alpha polypeptide is intended that the amino acid sequence of the polypeptide is identical to the reference sequence except that the polypeptide sequence may include up to five amino acid alterations per each 100 amino acids of the reference amino acid sequence of the endokine alpha polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 95%, 96%, 97%, 98% or 99% identical to, for instance, the amino acid sequence shown in FIG. 1A (SEQ ID NO:2) or to the amino acid sequence encoded by deposited cDNA clone can be determined conventionally using known computer programs such the BESTFIT program (Wisconsin Sequence Analysis Package, Version 8 for Unix, Genetics Computer Group, University Research Park, 575 Science Drive, Madison, Wis. 53711. When using BESTFIT or any other sequence alignment program to determine whether a particular sequence is, for instance, 95% identical to a reference sequence according to the present invention, the parameters are set, of course, such that the percentage of identity is calculated over the fall length of the reference amino acid sequence and that gaps in homology of up to 5% of the total number of amino acid residues in the reference sequence are allowed.

As described in detail below, the polypeptides of the present invention can be used to raise polyclonal and monoclonal antibodies, which are useful in diagnostic assays for detecting endokine alpha protein expression as described below or as agonists and antagonists capable of inhibiting endokine alpha protein function. Further, such polypeptides can be used in the yeast two-hybrid system to "capture" endokine alpha protein binding proteins which are also candidate agonist and antagonist according to the present invention. The yeast two hybrid system is described in Fields and Song, *Nature* 340:245–246 (1989).

In another aspect, the invention provides a peptide or polypeptide comprising an epitope-bearing portion of a polypeptide of the invention. The epitope of this polypeptide portion is an immunogenic or antigenic epitope of a polypeptide of the invention. An "immunogenic epitope" is defined as a part of a protein that elicits an antibody response when the whole protein is the immunogen. These immunogenic epitopes are believed to be confined to a few loci on the molecule. On the other hand, a region of a protein molecule to which an antibody can bind is defined as an "antigenic epitope." The number of immunogenic epitopes of a protein generally is less than the number of antigenic epitopes. See, for instance, Geysen, H. M. et al., *Proc. Natl. Acad. Sci. USA* 81:3998–4002 (1984).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G. et al., *Science* 219:660–666 (1983). Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. Peptides that are extremely hydrophobic and those of six or fewer residues generally are ineffective at inducing antibodies that bind to the mimicked protein; longer, soluble peptides, especially those containing proline residues, usually are effective. Sutcliffe et al., supra, at 661. For instance, 18 of 30 peptides designed according to these guidelines, containing 8–39 residues covering 75% of the sequence of the influenza virus hemagglutinin HA1 polypeptide chain induced antibodies that reacted with the HA1 protein or intact virus; and 12/12 peptides from the MuLV polymerase and 18/18 from the rabies glycoprotein induced antibodies that precipitated the respective proteins.

Antigenic epitope-bearing peptides and polypeptides of the invention are therefore useful to raise antibodies, including monoclonal antibodies, that bind specifically to a polypeptide of the invention. Thus, a high proportion of hybridomas obtained by fusion of spleen cells from donors immunized with an antigen epitope-bearing peptide generally secrete antibody reactive with the native protein. Sutcliffe et al., supra, at 663. The antibodies raised by antigenic epitope-bearing peptides or polypeptides are useful to detect the mimicked protein, and antibodies to different peptides may be used for tracking the fate of various regions of a protein precursor which undergoes posttranslational processing. The peptides and anti-peptide antibodies may be used in a variety of qualitative or quantitative assays for the mimicked protein, for instance in competition assays since it has been shown that even short peptides (e.g., about 9 amino acids) can bind and displace the larger peptides in immunoprecipitation assays. See, for instance, Wilson, I. A. et al., *Cell* 37:767–778 (1984) at 777. The anti-peptide antibodies of the invention also are useful for purification of the mimicked protein, for instance, by adsorption chromatography using methods well known in the art.

Antigenic epitope-bearing peptides and polypeptides of the invention designed according to the above guidelines preferably contain a sequence of at least seven, more preferably at least nine and most preferably between about 15 to about 30 amino acids contained within the amino acid sequence of a polypeptide of the invention. However, peptides or polypeptides comprising a larger portion of an amino acid sequence of a polypeptide of the invention, containing about 30 to about 50 amino acids, or any length up to and including the entire amino acid sequence of a polypeptide of the invention, also are considered epitope-bearing peptides or polypeptides of the invention and also are useful for inducing antibodies that react with the mimicked protein. Preferably, the amino acid sequence of the epitope-bearing peptide is selected to provide substantial solubility in aqueous solvents (i.e., the sequence includes relatively hydrophilic residues and highly hydrophobic sequences are preferably avoided); and sequences containing proline residues are particularly preferred.

Non-limiting examples of antigenic polypeptides that can be used to generate endokine-specific polyclonal and monoclonal antibodies include: a polypeptide comprising amino acid residues from about 44 to about 158 in FIG. 1A (SEQ ID NO:2); a polypeptide comprising amino acid residues from about 44 to about 54 in FIG. 1A (SEQ ID NO:2); a polypeptide comprising amino acid residues from about 57 to about 68 in FIG. 1A (SEQ ID NO:2); a polypeptide comprising amino acid residues from about 69 to about 78 in FIG. 1 (SEQ ID NO:2); a polypeptide comprising amino acid residues from about 94 to about 105 in FIG. 1A (SEQ ID NO:2); a polypeptide comprising amino acid residues from about 108 to about 132 in FIG. 1A (SEQ ID NO:2); and a polypeptide comprising amino acid residues from about 148 to about 158 in FIG. 1A (SEQ ID NO:2). As indicated above, the inventors have determined that the above polypeptide fragments are antigenic regions of the endokine alpha protein.

The epitope-bearing peptides and polypeptides of the invention may be produced by any conventional means for making peptides or polypeptides including recombinant means using nucleic acid molecules of the invention. For instance, a short epitope-bearing amino acid sequence may be fused to a larger polypeptide which acts as a carrier during recombinant production and purification, as well as during immunization to produce anti-peptide antibodies. Epitope-bearing peptides also may be synthesized using known methods of chemical synthesis. For instance, Houghten has described a simple method for synthesis of large numbers of peptides, such as 10–20 mg of 248 different 13 residue peptides representing single amino acid variants of a segment of the HA1 polypeptide which were prepared and characterized (by ELISA-type binding studies) in less than four weeks. See, Houghten, R. A., *Proc. Natl. Acad. Sci. USA* 82:5131–5135 (1985). This "Simultaneous Multiple Peptide Synthesis (SMPS)" process is further described in U.S. Pat. No. 4,631,211 to Houghten et al. (1986). In this procedure the individual resins for the solid-phase synthesis of various peptides are contained in separate solvent-permeable packets, enabling the optimal use of the many identical repetitive steps involved in solid-phase methods. A completely manual procedure allows 500–1000 or more syntheses to be conducted simultaneously. Houghten et al., supra, at 5134.

Epitope-bearing peptides and polypeptides of the invention are used to induce antibodies according to methods well known in the art. See, for instance, Sutcliffe et al., supra; Wilson et al., supra; Chow, M. et al., *Proc. Natl. Acad. Sci. USA* 82:910–914; and Bittle, F. J. et al., *J. Gen. Virol.* 66:2347–2354 (1985). Generally, animals may be immunized with free peptide; however, anti-peptide antibody titer may be boosted by coupling of the peptide to a macromolecular carrier, such as keyhole limpet hemocyanin (KLH) or tetanus toxoid. For instance, peptides containing cysteine may be coupled to carrier using a linker such as m-maleimidobenzoyl-N-hydroxysuccinimide ester (MBS), while other peptides may be coupled to carrier using a more general linking agent such as glutaraldehyde.

Animals such as rabbits, rats and mice are immunized with either free or carrier-coupled peptides, for instance, by intraperitoneal and/or intradermal injection of emulsions containing about 100 µg peptide or carrier protein and Freund's adjuvant. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

Immunogenic epitope-bearing peptides of the invention, i.e., those parts of a protein that elicit an antibody response when the whole protein is the immunogen, are identified according to methods known in the art. For instance, Geysen et al. (1984), supra, discloses a procedure for rapid concurrent synthesis on solid supports of hundreds of peptides of sufficient purity to react in an enzyme-linked immunosorbent assay. Interaction of synthesized peptides with antibodies is then easily detected without removing them from the support. In this manner a peptide bearing an immunogenic epitope of a desired protein may be identified routinely by one of ordinary skill in the art.

For instance, the immunologically important epitope in the coat protein of foot-and-mouth disease virus was located by Geysen et al. with a resolution of seven amino acids by synthesis of an overlapping set of all 208 possible hexapeptides covering the entire 213 amino acid sequence of the protein. Then, a complete replacement set of peptides in which all 20 amino acids were substituted in turn at every position within the epitope were synthesized, and the particular amino acids conferring specificity for the reaction with antibody were determined. Thus, peptide analogs of the epitope-bearing peptides of the invention can be made routinely by this method. U.S. Pat. No. 4,708,781 to Geysen (1987) further describes this method of identifying a peptide bearing an immunogenic epitope of a desired protein.

Further still, U.S. Pat. No. 5,194,392 to Geysen (1990) describes a general method of detecting or determining the sequence of monomers (amino acids or other compounds) which is a topological equivalent of the epitope (i.e., a "mimotope") which is complementary to a particular paratope (antigen binding site) of an antibody of interest. More generally, U.S. Pat. No. 4,433,092 to Geysen (1989) describes a method of detecting or determining a sequence of monomers which is a topographical equivalent of a ligand which is complementary to the ligand binding site of a particular receptor of interest. Similarly, U.S. Pat. No. 5,480,971 to Houghten, R. A. et al. (1996) on Peralkylated Oligopeptide Mixtures discloses linear $C_1$–$C_7$-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods.

The present inventors have discovered that the endokine alpha protein is a 169 residue protein exhibiting three main structural domains. The intracellular domain was identified within residues from about 1 to about 17 in FIG. 1A (SEQ ID NO:2). The transmembrane domain was identified within residues from about 18 to about 43 in FIG. 1A (SEQ ID NO:2). The extracellular domain was identified within residues from about 44 to about 169 in FIG. 1A (SEQ ID NO:2). Thus, the invention further provides preferred endokine alpha protein fragments comprising a polypeptide selected from: the endokine alpha intracellular domain, the transmembrane domain and the endokine alpha extracellular domain.

The extracellular domain of the endokine alpha protein can be combined with parts of the constant domain of immunoglobulins (IgG), resulting in chimeric polypeptides. These fusion proteins show an increased half-life in vivo. This has been shown, e.g., for chimeric proteins consisting of the first two domains of the human CD4-polypeptide and various domains of the constant regions of the heavy or light chains of mammalian immunoglobulins (EP A 394,827; Traunecker et al., *Nature* 331:84–86 (1988)). Fusion proteins that have a disulfide-linked dimeric structure due to the IgG part can also be more efficient in binding and neutralizing the ligands than the monomeric extracellular domains alone (Fountoulakis et al., *J. Biochem.* 270:3958–3964 (1995)).

The entire disclosure of each document cited in this section on "Polypeptides and Peptides" is hereby incorporated herein by reference.

Endokine Alpha Related Disorder Diagnosis

Endokine alpha is a new member of the TNF family of cytokines. For endokine alpha related disorders, it is believed that substantially altered (increased or decreased) levels of endokine alpha gene expression can be detected in tissue or other cells or bodily fluids (e.g., sera, plasma, urine, synovial fluid or spinal fluid) taken from an individual having such a disorder, relative to a "standard" endokine alpha gene expression level, that is, the endokine alpha expression level in tissue or bodily fluids from an individual not having the disorder. Thus, the invention provides a diagnostic method useful during diagnosis of an endokine alpha-related disorder, which involves measuring the expression level of the gene encoding the endokine alpha protein in tissue or other cells or body fluid from an individual and comparing the measured gene expression level with a standard endokine alpha gene expression level, whereby an increase or decrease in the gene expression level compared to the standard is indicative of an endokine alpha related disorder.

By individual is intended mammalian individuals, preferably humans. By "measuring the expression level of the gene encoding the endokine alpha protein" is intended qualitatively or quantitatively measuring or estimating the level of the endokine alpha protein or the level of the mRNA encoding the endokine alpha protein in a first biological sample either directly (e.g., by determining or estimating absolute protein level or mRNA level) or relatively (e.g., by comparing to the endokine alpha protein level or mRNA level in a second biological sample). Preferably, the endokine alpha protein level or mRNA level in the first biological sample is measured or estimated and compared to a standard endokine alpha protein level or mRNA level, the standard being taken from a second biological sample obtained from an individual not having the disorder or being determined by averaging levels from a population of individuals not having a disorder involving endokine alpha. As will be appreciated in the art, once a standard endokine alpha protein level or mRNA level is known, it can be used repeatedly as a standard for comparison.

By "biological sample" is intended any biological sample obtained from an individual, body fluid, cell line, tissue culture, or other source which contains endokine alpha protein or mRNA. As indicated, biological samples include body fluids (such as sera, plasma, urine, synovial fluid and spinal fluid) which contain secreted mature endokine alpha protein, or tissue sources found to express endokine alpha. Methods for obtaining tissue biopsies and body fluids from mammals are well known in the art. Where the biological sample is to include mRNA, a tissue biopsy is the preferred source.

The present invention is useful for diagnosis of various endokine alpha-related disorders in mammals, preferably humans, as similar to TNF-like disorders known in the art or as presented herein. These include disorders associated with immunomodulation and inflammation, cell proliferation, angiogenesis, tumor metastases, apoptosis, sepsis and endotoxemia.

Total cellular RNA can be isolated from a biological sample using any suitable technique such as the single-step-guanidinium-thiocyanate-phenol-chloroform method described in Chomczynski and Sacchi, *Anal. Biochem.* 162:156–159 (1987). Levels of mRNA encoding an endokine alpha polypeptide are then assayed using any appropriate method. These include Northern blot analysis, S1 nuclease mapping, the polymerase chain reaction (PCR), reverse transcription in combination with the polymerase chain reaction (RT-PCR), and reverse transcription in combination with the ligase chain reaction (RT-LCR).

Northern blot analysis can be performed as described in Harada et al., *Cell* 63:303–312 (1990). Briefly, total RNA is prepared from a biological sample as described above. For the Northern blot, the RNA is denatured in an appropriate buffer (such as glyoxal/dimethyl sulfoxide/sodium phosphate buffer), subjected to agarose gel electrophoresis, and transferred onto a nitrocellulose filter. After the RNAs have been linked to the filter by a UV linker, the filter is prehybridized in a solution containing formamide, SSC, Denhardt's solution, denatured salmon sperm, SDS, and sodium phosphate buffer. Endokine alpha protein cDNA labeled according to any appropriate method (such as the $^{32}$P-multiprimed DNA labeling system (Amersham)) is used as probe. After hybridization overnight, the filter is washed and exposed to x-ray film. cDNA for use as probe according to the present invention is described in the sections above and will preferably at least 15 bp in length.

S1 mapping can be performed as described in Fujita et al., *Cell* 49:357–367 (1987). To prepare probe DNA for use in S1 mapping, the sense strand of above-described cDNA is used as a template to synthesize labeled antisense DNA. The antisense DNA can then be digested using an appropriate restriction endonuclease to generate further DNA probes of a desired length. Such antisense probes are useful for visualizing protected bands corresponding to the target mRNA (i.e., mRNA encoding the endokine alpha protein). Northern blot analysis can be performed as described above.

Preferably, levels of mRNA encoding the endokine alpha protein are assayed using the RT-PCR method described in Makino et al., *Technique* 2:295–301 (1990). By this method, the radioactivities of the "amplicons" in the polyacrylamide gel bands are linearly related to the initial concentration-of the target mRNA. Briefly, this method involves adding total RNA isolated from a biological sample in a reaction mixture containing a RT primer and appropriate buffer. After incubating for primer annealing, the mixture can be supplemented with a RT buffer, dNTPs, DTT, RNase inhibitor and reverse transcriptase. After incubation to achieve reverse transcription of the RNA, the RT products are then subject to PCR using labeled primers. Alternatively, rather than labeling the primers, a labeled dNTP can be included in the PCR reaction mixture. PCR amplification can be performed in a DNA thermal cycler according to conventional techniques. After a suitable number of rounds to achieve amplification, the PCR reaction mixture is electrophoresed on a polyacrylamide gel. After drying the gel, the radioactivity of the appropriate bands (corresponding to the mRNA encoding the endokine alpha protein) is quantified using an imaging analyzer. RT and PCR reaction ingredients and conditions, reagent and gel concentrations, and labeling methods are well known in the art. Variations on the RT-PCR method will be apparent to the skilled artisan.

Any set of oligonucleotide primers which will amplify reverse transcribed target mRNA can be used and can be designed as described in the sections above.

Assaying endokine alpha protein levels in a biological sample can occur using any art-known method. Preferred for assaying endokine alpha protein levels in a biological sample are antibody-based techniques. For example, endokine alpha protein expression in tissues can be studied with classical immunohistological methods. In these, the specific recognition is provided by the primary antibody (polyclonal or monoclonal) but the secondary detection system can utilize fluorescent, enzyme, or other conjugated secondary antibodies. As a result, an immunohistological staining of tissue section for pathological examination is obtained. Tissues can also be extracted, e.g., with urea and neutral detergent, for the liberation of endokine alpha protein for Western-blot or dot/slot assay (Jalkanen, M., et al., *J. Cell. Biol.* 101:976–985 (1985); Jalkanen, M., et al., *J. Cell. Biol.* 105:3087–3096 (1987)). In this technique, which is based on the use of cationic solid phases, quantitation of endokine alpha protein can be accomplished using isolated endokine alpha protein as a standard. This technique can also be applied to body fluids. With these samples, a molar concentration of endokine alpha protein will aid to set standard values of endokine alpha protein content for different body fluids, like serum plasma, urine, synovial fluid, spinal fluid, etc. The normal appearance of endokine alpha protein amounts can then be set using values from healthy individuals, which can be compared to those obtained from a test subject.

Other antibody-based methods useful for detecting endokine alpha protein levels include immunoassays, such as the enzyme linked immunosorbent assay (ELISA) and the radioimmunoassay (RIA). For example, endokine alpha protein-specific monoclonal antibodies can be used both as an immunoadsorbent and as an enzyme-labeled probe to detect and quantify the endokine alpha protein. The amount of endokine alpha protein present in the sample can be calculated by reference to the amount present in a standard preparation using a linear regression computer algorithm. Such an ELISA for detecting a tumor antigen is described in Iacobelli et al., *Breast Cancer Research and Treatment* 11:19–30 (1988). In another ELISA assay, two distinct specific monoclonal antibodies can be used to detect endokine alpha protein in a body fluid. In this assay, one of the antibodies is used as the immunoadsorbent and the other as the enzyme-labeled probe.

The above techniques may be conducted essentially as a "one-step" or "two-step" assay. The "one-step" assay involves contacting endokine alpha protein with immobilized antibody and, without washing, contacting the mixture with the labeled antibody. The "two-step" assay involves washing before contacting the mixture with the labeled antibody. Other conventional methods may also be employed as suitable. It is usually desirable to immobilize one component of the assay system on a support, thereby allowing other components of the system to be brought into contact with the component and readily removed from the sample.

Suitable enzyme labels include, for example, those from the oxidase group, which catalyze the production of hydrogen peroxide by reacting with substrate. Glucose oxidase is particularly preferred as it has good stability and its substrate (glucose) is readily available. Activity of an oxidase label may be assayed by measuring the concentration of hydrogen peroxide formed by the enzyme-labeled antibody/substrate reaction. Besides enzymes, other suitable labels include radioisotopes, such as iodine ($^{125}I$, $^{121}I$), carbon ($^{14}C$), sulfur (35S), tritium ($^3H$), indium ($^{112}In$), and technetium ($^{99m}Tc$), and fluorescent labels, such as fluorescein and rhodamine, and biotin.

In addition to assaying endokine alpha protein levels in a biological sample obtained from an individual, endokine alpha protein can also be detected in vivo by imaging. Antibody labels or markers for in vivo imaging of endokine alpha protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A endokine alpha protein-specific antibody or antibody portion which has been labeled with an appropriate detectable imaging moiety, such as a radioisotope (for example, $^{131}I$, $^{111}In$, $^{99m}Tc$), a radio-opaque substance, or a material detectable by nuclear magnetic resonance, is introduced (for example, parenterally, subcutaneously or intraperitoneally) into the mammal to be examined for a disorder. It will be understood in the art that the size of the subject and the imaging system used will determine the quantity of imaging moieties needed to produce diagnostic images. In the case of a radioisotope moiety, for a human subject, the quantity of radioactivity injected will normally range from about 5 to 20 millicuries of $^{99m}Tc$. The labeled antibody or antibody portion will then preferentially accumulate at the location of cells which contain endokine alpha protein. In vivo tumor imaging is described in S. W. Burchiel et al., "Immunopharmacokinetics of Radiolabeled Antibodies and Their Portions" (Chapter 13 in *Tumor Imaging: The Radiochemical Detection of Cancer*, Burchiel, S. W. and Rhodes, B. A. eds., Masson Publishing Inc. (1982)).

Endokine alpha-protein specific antibodies for use in the present invention can be raised against the intact endokine alpha protein or an antigenic polypoptide portion thereof, which may presented together with a carrier protein, such as an albumin, to an animal system (such as rabbit or mouse) or, if it is long enough (at least about 25 amino acids), without a carrier.

As used herein, the term "antibody" (Ab) or "monoclonal antibody" (Mab) is meant to include intact molecules as well as antibody portions (such as, for example, Fab and F(ab')$_2$ portions) which are capable of specifically binding to endokine alpha protein. Fab and F(ab')$_2$ portions lack the Fc portion of intact antibody, clear more rapidly from the circulation, and may have less non-specific tissue binding of an intact antibody (Wahl et al., *J. Nucl. Med.* 24:316–325 (1983)). Thus, these portions are preferred.

The antibodies of the present invention may be prepared by any of a variety of methods. For example, cells expressing the endokine alpha protein or an antigenic portion thereof can be administered to an animal in order to induce the production of sera containing polyclonal antibodies. In a preferred method, a preparation of endokine alpha protein is prepared and purified as described above to render it substantially free of natural contaminants. Such a preparation is then introduced into an animal in order to produce polyclonal antisera of greater specific activity.

In the most preferred method, the antibodies of the present invention are monoclonal antibodies (or endokine alpha protein binding portions thereof). Such monoclonal antibodies can be prepared using hybridoma technology (see, e.g., Colligan, *Current Protocols in Immunology,* Wiley Interscience, New York (1990–1996); Harlow & Lane, *Antibodies: A Laboratory Manual,* Chs. 6–9, Cold Spring Harbor Press, Cold Spring Harbor, N.Y. (1988); Ausubel, infra, at Chapter 11, these references entirely incorporated herein by reference).

In general, such procedures involve immunizing an animal (preferably a mouse) with an endokine alpha polypeptide antigen or with an endokine alpha polypeptide-expressing cell. Suitable cells can be recognized by their capacity to bind anti-endokine alpha protein antibody. Such cells may be cultured in any suitable tissue culture medium (e.g., Earle's modified Eagle's medium supplemented with 10% fetal bovine serum (inactivated at about 56° C.), supplemented with about 10 µg/l of nonessential amino acids, about 1,000 g/ml of penicillin, and about 100 µg/ml of streptomycin). The splenocytes of such mice are extracted and fused with a suitable myeloma cell line. Any suitable myeloma cell line may be employed in accordance with the present invention (e.g., parent myeloma cell line (SP$_2$O), available from the American Type Culture Collection (ATCC) (Manassas, Va., USA)). After fusion, the resulting hybridoma cells are selectively maintained in HAT medium, and then cloned by limiting dilution as described by Wands et al., *Gastroenterology* 80:225–232 (1981); Harlow & Lane, infra, Chapter 7. The hybridoma cells obtained through such a selection are then assayed to identify clones which secrete antibodies capable of binding the endokine alpha antigen.

Alternatively, additional antibodies capable of binding to the endokine alpha protein antigen may be produced in a two-step procedure through the use of anti-idiotypic antibodies. Such a method makes use of the fact that antibodies are themselves antigens, and therefore it is possible to obtain an antibody which binds to a second antibody. In accordance with this method, endokine alpha protein specific antibodies are used to immunize an animal, preferably a mouse. The splenocytes of such an animal are then used to produce hybridoma cells, and the hybridoma cells are screened to identify clones which produce an antibody whose ability to bind to the endokine alpha protein-specific antibody can be blocked by the endokine alpha protein antigen. Such antibodies comprise anti-idiotypic antibodies to the endokine alpha protein-specific antibody and can be used to immunize an animal to induce formation of further endokine alpha protein-specific antibodies.

It will be appreciated that Fab and F(ab')$_2$ and other portions of the antibodies of the present invention may be used according to the methods disclosed herein. Such portions are typically produced by proteolytic cleavage, using enzymes such as papain (to produce Fab portions) or pepsin (to produce F(ab')$_2$ portions). Alternatively, endokine alpha protein-binding portions can be produced through the application of recombinant DNA technology or through synthetic chemistry.

Where in vivo imaging is used to detect enhanced levels of endokine alpha protein for diagnosis in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art. See, for review, Morrison, *Science* 229:1202 (1985); Oi et al., *BioTechniques* 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., *Nature* 312:643 (1984); Neuberger et al., *Nature* 314:268 (1985).

Further suitable labels for the endokine alpha protein-specific antibodies of the present invention are provided below. Examples of suitable enzyme labels include malate dehydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, and acetylcholine esterase.

Examples of suitable radioisotopic labels include $^3$H, $^{111}$In, $^{125}$I, $^{131}$I, $^{32}$P, $^{35}$S, $^{14}$C, $^{51}$Cr, $^{57}$To, $^{58}$Co, $^{59}$Fe, $^{75}$Se, $^{152}$Eu, $^{90}$Y, $^{67}$Cu, $^{217}$Ci, $^{211}$At, $^{212}$Pb, $^{47}$Sc, $^{109}$Pd, etc. $^{111}$In and $^{99m}$Tc are preferred isotopes where in vivo imaging is used since they avoid the problem of dehalogenation of the $^{125}$I or $^{131}$I-labeled monoclonal antibody by the liver. In addition, these radionucleotides have a more favorable gamma emission energy for imaging (Perkins et al., Eur. *J. Nucl. Med.* 10:296–301 (1985); Carasquillo et al., *J. Nucl. Med.* 28:281–287 (1987)). For example, $^{111}$In coupled to monoclonal antibodies with 1-(p-isothiocyanatobenzyl)-DPTA has shown little uptake in non-tumorous tissues, particularly the liver, and therefore enhances specificity of tumor localization (Esteban et al., *J. Nucl. Med.* 28:861–870 (1987)).

Examples of suitable non-radioactive isotopic labels include $^{157}$Gd, 55Mn, $^{162}$Dy, $^{52}$Tr, and $^{56}$Fe.

Examples of suitable fluorescent labels include an $^{152}$Eu label, a fluorescein label, an isothiocyanate label, a rhodamine label, a phycoerythrin label, a phycocyanin label, an allophycocyanin label, an o-phthaldehyde label, and a fluorescamine label.

Examples of suitable toxin labels include diphtheria toxin, ricin, and cholera toxin.

Examples of chemiluminescent labels include a luminal label, an isoluminal label, an aromatic acridinium ester label, an imidazole label, an acridinium salt label, an oxalate ester label, a luciferin label, a luciferase label, and an aequorin label.

Examples of nuclear magnetic resonance contrasting agents include heavy metal nuclei such as Gd, Mn, and Fe.

Typical techniques for binding the above-described labels to antibodies are provided by Kennedy et al. (*Clin. Chim. Acta* 70:1–31 (1976)), and Schurs et al. (*Clin. Chim. Acta* 81:1–40 (1977)). Coupling techniques mentioned in the latter are the glutaraldehyde method, the periodate method, the dimaleimide method, the m-maleimidobenzyl-N-hydroxy-succinimide ester method, all of which methods are incorporated by reference herein.

Chromosome Assays

The nucleic acid molecules of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

In certain preferred embodiments in this regard, the cDNA herein disclosed is used to clone genomic DNA of an endokine alpha protein gene. This can be accomplished using a variety of well known techniques and libraries, which generally are available commercially. The genomic DNA then is used for in situ chromosome mapping using well known techniques for this purpose. Typically, in accordance with routine procedures for chromosome mapping, some trial and error may be necessary to identify a genomic probe that gives a good in situ hybridization signal.

In some cases, in addition, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified portion.

PCR mapping of somatic cell hybrids is a rapid procedure for assigning a particular DNA to a particular chromosome. Using the present invention with the same oligonucleotide primers, sublocalization can be achieved with panels of portions from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization ("FISH") of a cDNA clone to a metaphase chromosomal spread can be used to provide a precise chromosomal location in one step. This technique can be used with probes from the cDNA as short as 50 or 60 bp. For a review of this technique, see Verma et al., *Human Chromosomes: A Manual of Basic Techniques*, Pergamon Press, New York (1988).

Once a sequence has been mapped to a precise chromosomal location, the physical position of the sequence on the chromosome can be correlated with genetic map data. Such data are found, for example, in V. McKusick, *Mendelian Inheritance in Man*, available on-line through Johns Hopkins University, Welch Medical Library. The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

Endokine Alpha Protein and Antibody Therapy

As indicated above, TNF is noted for its pro-inflammatory actions which result in tissue injury, such as induction of procoagulant activity on vascular endothelial cells (Pober, J. S. et al., *J. Immunol.* 136:1680 (1986)), increased adherence of neutrophils and lymphocytes (Pober, J. S. et al., *J. Immunol.* 138:3319 (1987)), and stimulation of the release of platelet activating factor from macrophages, neutrophils and vascular endothelial cells (Camussi, G. et al., *J. Exp. Med.* 166:1390 (1987)). Recent evidence implicates TNF in the pathogenesis of many infections (Cerami, A. et al., *Immunol. Today* 9:28 (1988)), immune disorders, neoplastic pathology, e.g., in cachexia accompanying some malignancies (Oliff, A. et al., *Cell* 50:555 (1987)), and in autoimmune pathologies and graft-versus host pathology (Piguet, P.-F. et al., *J. Exp. Med* 166:1280 (1987)). A number of studies have suggested that TNF is an important mediator of the cachexia in cancer, infectious pathology, and in other catabolic states.

Thus, the endokine alpha protein of the present invention can be used for tumor targeting, preferably, after conjugation with radioisotopes or cytostatic drugs (Gruss and Dower, *Blood* 85(12):3378–3404 (1995)). Endokine alpha can be used in patients with melanoma and sarcoma for tumor regression and extension of patient life span through a local injection or used in isolated limb perfusion (Aggarwal and Natarajan, *Eur. Cytokine Netw.* 7(2):92–124 (1996)).

The endokine alpha of the present invention can also have a therapeutic role in specific situations, for example, activity against viral, bacterial, yeast, fungal, and other infections (including toxoplasma gondii, schistosoma mansoni, listeria monocytogens and BCG). These effects of endokine alpha can be indirect and thus preferably, mediated through activation of macrophages, eosinophils, fibroblasts, or neutrophils.

TNF is also thought to play a central role in the pathophysiological consequences of Gram-negative sepsis and endotoxic shock (Michie, H. R. et al., *Br. J. Surg.* 76:670–671 (1989); Debets, J. M. H. et al., *Second Vienna Shock Forum*, p. 463–466 (1989); Simpson, S. Q. et al., *Crit. Care Clin.* 5:27-47 (1989)), including fever, malaise, anorexia, and cachexia. Endotoxin is a potent monocyte/macrophage activator which stimulates production and secretion of TNF (Kornbluth, S. K. et al., *J. Immunol.* 137:2585–2591 (1986)) and other cytokines. Elevated levels of circulating TNF have also been found in patients suffering from Gram-negative sepsis (Waage, A. et al., *Lancet* 1:355–357 (1987); Hammerle, A. F. et al., *Second Vienna Shock Forum* p. 715–718 (1989); Debets, J. M. H. et al., *Crit. Care Mect* 17:489–497 (1989); Calandra, T. et al., *J. Infec. Dis.* 161:982–987 (1990)).

Neutralizing antisera or mAbs to TNF have been shown in mammals other than man to abrogate adverse physiological changes and prevent death after lethal challenge in experimental endotoxemia and bacteremia. This effect has been demonstrated, e.g., in rodent lethality assays and in primate pathology model systems (Mathison, J. C. et al., *J. Clin. Invest.* 81:1925–1937 (1988); Beutler, B. et al., *Science* 229:869–871 (1985); Tracey, K. J. et al., *Nature* 330:662–664 (1987); Shimamoto, Y. et al., *Immunol. Lett.* 17:311–318 (1988); Silva, A. T. et al., *J. Infect Dis.* 162:421–427 (1990); Opal, S. M. et al., *J. Infect. Dis.* 161:1148–1152 (1990); Hinshaw, L. B. et al., *Circ. Shock* 30:279–292 (1990)). To date, experience with anti-TNF mAb therapy in humans has been limited but shows beneficial therapeutic results, e.g., in arthritis and sepsis. See, e.g., Elliott, M. J. et al., *Baillieres Clin. Rheumatol.* 9:633–52 (1995); Feldmann M, et al., *Ann. N. Y. Acad. Sci. USA* 766:272–8 (1995); van der Poll, T. et al., *Shock* 3:1–12 (1995); Wherry et al., *Crit. Care. Med.* 21:S436–40 (1993); Tracey K. J., et al., *Crit. Care Med* 21:S415–22 (1993).

As endokine alpha is believed to exhibit many of the biological effects of TNF, the present invention is further directed to antibody-based therapies which involve administering an anti-endokine alpha antibody to a mammalian, preferably human, patient for treating one or more of the above-described disorders. Methods for producing anti-endokine alpha polyclonal and monoclonal antibodies are described in detail above. Such antibodies may be provided in pharmaceutically acceptable compositions as known in the art or as described herein.

A summary of the ways in which the antibodies of the present invention may be used therapeutically includes binding endokine alpha locally or systemically in the body or by direct cytotoxicity of the antibody, e.g., as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

The pharmaceutical compositions of the present invention may be administered by any means that achieve their intended purpose. Amounts and regimens for the administration of antibodies, their fragments or derivatives can be determined readily by those with ordinary skill in the clinical art of treating TNF-related disease.

For example, administration may be by parenteral, subcutaneous, intra-venous, intramuscular, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired.

Compositions within the scope of this invention include all compositions wherein the antibody, fragment or derivative is contained in an amount effective to achieve its intended purpose. While individual needs vary, determination of optimal ranges of effective amounts of each component is within the skill of the art. The effective dose is a function of the individual chimeric or monoclonal antibody, the presence and nature of a conjugated therapeutic agent (see below), the patient and his clinical status, and can vary from about 10 μg/kg body weight to about 5000 mg/kg body weight. The preferred dosages comprise 0.1 to 500 mg/kg body wt.

In addition to the pharmacologically active compounds, the new pharmaceutical compositions may contain suitable pharmaceutically acceptable carriers comprising excipients and auxiliaries which facilitate processing of the active compounds into preparations which can be used pharmaceutically. Preferably, the preparations contain from about 0.01 to 99 percent, preferably from about 20 to 75 percent of active compound(s), together with the excipient.

Similarly, preparations of an endokine alpha antibody or fragment of the present invention for parenteral administration, such as in detectably labeled form for imaging or in a free or conjugated form for therapy, include sterile aqueous or non-aqueous solutions, suspensions, and emulsions. Examples of non-aqueous solvents are propylene glycol, polyethylene glycol, vegetable oil such as olive oil, and injectable organic esters such as ethyl oleate. Aqueous carriers include water, alcoholic/aqueous solutions, emulsions or suspensions, including saline and buffered media, parenteral vehicles including sodium chloride solution, Ringer's dextrose, dextrose and sodium chloride, lactated Ringer's, or fixed oils. Intravenous vehicles include fluid and nutrient replenishers, such as those based on Ringer's dextrose, and the like. Preservatives and other additives may also be present, such as, for example, antimicrobials, antioxidants, chelating agents, and inert gases and the like. See, generally, *Remington's Pharmaceutical Science,* 16th ed., Mack Publishing Co., Easton, Pa., 1980.

In particular, the antibodies, fragments and derivatives of the present invention are useful for treating a subject having or developing endokine alpha related disorders as described herein. Such treatment comprises parenterally administering single or multiple doses of the antibody, a fragment or derivative, or a conjugate thereof.

The antibodies of this invention may be advantageously utilized in combination with other monoclonal or chimeric antibodies, or with lymphokines or hemopoietic growth factors, etc., which serve to increase the number or activity of effector cells which interact with the antibodies.

Since circulating concentrations of endokine alpha (like TNF) tend to be extremely low, in the range of about 10 pg/ml in non-septic individuals, and reaching about 50 pg/ml in septic patients and above 100 pg/ml in the sepsis syndrome for TNF (Hammerle, A. F. et al., 1989, supra) or may be only be detectable at sites of endokine alpha-related disorders, it is preferred to use high affinity and/or potent in vivo endokine alpha-inhibiting and/or neutralizing antibodies, fragments or regions thereof, for both endokine alpha immunoassays and therapy of endokine related disorders. Such antibodies, fragments, or regions, will preferably have an affinity for human endokine alpha, expressed as Ka, of at least $10^8$ $M^{-1}$, more preferably, at least $10^9$ $M^{-1}$, such as $5 \times 10^8$ $M^{-1}$, $8 \times 10^8$ $M^{-1}$, $2 \times 10^9$ $M^{-1}$, $4 \times 10^9$ $M^{-1}$, $6 \times 10^9$ $M^{-1}$, $8 \times 10^9$ $M^{-1}$.

Preferred for human therapeutic use are high affinity murine and murine/human or human/human chimeric antibodies, and fragments, regions and derivatives having potent in vivo endokine-inhibiting and/or neutralizing activity, according to the present invention, e.g., that block endokine-induced IL-1, IL-6 or TNF secretion, procoagulant activity, expression of cell adhesion molecules such as ELAM-1 and ICAM-1 and mitogenic activity, in vivo, in situ, and in vitro.

Having generally described the invention, the same will be more readily understood by reference to the following examples, which are provided by way of illustration and are not intended as limiting.

EXAMPLES

Example 1

Expression and Purification of Endokine Alpha in *E. coli*

The DNA sequence encoding the endokine alpha protein in the deposited cDNA clone is amplified using PCR oligonucleotide primers specific to the amino terminal sequences of the endokine alpha protein. Additional nucleotides containing restriction sites to facilitate cloning are added to the 5' and 3' sequences, respectively.

The 5' oligonucleotide primer has the sequence GCG CCA TGG CTA AGT TTG GAC CAT (SEQ ID NO:5) containing the underlined Nco I restriction site.

The 3' primer has the sequence GCG AAG CTT TCA AGT CTC TAG GAG ATG (SEQ ID NO:6) containing the underlined HindIII restriction site.

The restriction sites are convenient to restriction enzyme sites in the bacterial expression vector pQE60, which is used for bacterial expression in M15/rep4 host cells in these examples. (Qiagen, Inc., Chatsworth, Calif., 91311). pQE60 encodes ampicillin antibiotic resistance ("Amp$^r$") and contains a bacterial origin of replication ("ori"), an IPTG inducible promoter, a ribosome binding site ("RBS"), a 6-His tag and restriction enzyme sites.

The amplified endokine alpha protein DNA and the vector pQE60 both are digested with NcoI and HindIII and the digested DNAs are then ligated together. Insertion of the endokine alpha protein DNA into the restricted pQE60 vector places the endokine alpha protein coding region downstream of and operably linked to the vector's IPTG-inducible promoter and in-frame with an initiating ATG appropriately positioned for translation of endokine alpha protein.

The ligation mixture is transformed into competent *E. coli* cells using standard procedures. Such procedures are described in Sambrook et al., *Molecular Cloning: A Laboratory Manual*, 2nd Ed.; Cold Spring Harbor Laboratory Press, Cold Spring Harbor, N.Y. (1989). *E. coli* strain M15/rep4, containing multiple copies of the plasmid pREP4, which expresses lac repressor and confers kanamycin resistance ("Kan$^r$"), is used in carrying out the illustrative example described here. This strain, which is only one of many that are suitable for expressing endokine alpha protein, is available commercially from Qiagen.

Transformants are identified by their ability to grow on LB plates in the presence of ampicillin and kanamycin. Plasmid DNA is isolated from resistant colonies and the identity of the cloned DNA confirmed by restriction analysis.

Clones containing the desired constructs are grown overnight ("O/N") in liquid culture in LB media supplemented with both ampicillin (100 μg/ml) and kanamycin (25 μg/ml).

The O/N culture is used to inoculate a large culture, at a dilution of approximately 1:100 to 1:250. The cells are grown to an optical density at 600 NM ("OD600") of between 0.4 and 0.6. Isopropyl-B-D-thiogalactopyranoside ("IPTG") is then added to a final concentration of 1 mM to induce transcription from lac repressor sensitive promoters, by inactivating the lacI repressor. Cells subsequently are incubated further for 3 to 4 hours. Cells then are harvested by centrifugation and disrupted, by standard methods. Inclusion bodies are purified from the disrupted cells using routine collection techniques, and protein is solubilized from the inclusion bodies into 8M urea. The 8M urea solution containing the solubilized protein is passed over a PD-10 column in 2×phosphate-buffered saline ("PBS"), thereby removing the urea, exchanging the buffer and refolding the protein. The protein is purified by a further step of chromatography to remove endotoxin. Then, it is sterile filtered. The sterile filtered protein preparation is stored in 2×PBS.

Example 2

Cloning and Expression of Endokine Alpha in a Baculovirus Expression System

The cDNA sequence encoding the endokine alpha protein in the deposited clone is amplified using PCR oligonucleotide primers corresponding to 5' and 3' regions of the gene.

The 5' primer has the sequence GC GGA TCC CGA GAC TGC TAA GGA GCC (SEQ ID NO:7) containing the underlined BamHI restriction enzyme site and containing nucleotides encoding a portion of the endokine alpha protein in FIG. 1A.

The 3' primer has the sequence GC GGA TCC CTA GGA GAT GAA TTG GGG ATT TG (SEQ ID NO:8) containing the underlined BamHI restriction site and containing a sequence complementary to that encoding a portion of the endokine alpha protein in FIG. 1A.

The amplified fragment is isolated from a 1% agarose gel using a commercially available kit ("Geneclean," BIO 101 Inc., La Jolla, Calif.). The fragment then is digested with BamHI and again is purified on a 1% agarose gel. This fragment is designated herein F2.

The vector pA2-GP is used to express the endokine alpha protein in the baculovirus expression system, using standard methods, as described in Summers et al., *A Manual of Methods for Baculovirus Vectors and Insect Cell Culture Procedures*, Texas Agricultural Experimental Station Bulletin No. 1555 (1987). This expression vector contains the strong polyhedrin promoter of the *Autographa californica* nuclear polyhedrosis virus (AcMNPV) followed by convenient restriction sites. The signal peptide of AcMNPV gp67, including the N-terminal methionine, is located just upstream of a BamHI site. The polyadenylation site of the simian virus 40 ("SV40") is used for efficient polyadenylation. For an easy selection of recombinant virus, the beta-galactosidase gene from *E. coli* is inserted in the same orientation as the polyhedrin promoter and is followed by the polyadenylation signal of the polyhedrin gene. The polyhedrin sequences are flanked at both sides by viral sequences for cell-mediated homologous recombination with wild-type viral DNA to generate viable virus that express the cloned polynucleotide.

Many other baculovirus vectors could be used in place of pA2-GP, such as pAc373, pVL941 and pAcIM1 provided, as those of skill readily will appreciate, that construction provides appropriately located signals for transcription, translation, trafficking and the like, such as an in-frame AUG and a signal peptide, as required. Such vectors are described in Luckow et al., *Virology* 170: 31–39, among others.

The plasmid is digested with the restriction enzyme BamHI and then is dephosphorylated using calf intestinal phosphatase, using routine procedures known in the art. The DNA is then isolated from a 1% agarose gel using a commercially available kit ("Geneclean" BIO 101 Inc., La Jolla, Calif.). This vector DNA is designated herein "V2".

Fragment F2 and the dephosphorylated plasmid V2 are ligated together with T4 DNA ligase. *E. coli* HB 101 cells are transformed with ligation mix and spread on culture plates. Bacteria are identified that contain the plasmid with the human endokine alpha gene by digesting DNA from individual colonies using BamHI and then analyzing the digestion product by gel electrophoresis. The sequence of the cloned fragment is confirmed by DNA sequencing.

5 μg of the plasmid is co-transfected with 1.0 μg of a commercially available linearized baculovirus DNA ("BaculoGold™ baculovirus DNA", Pharmingen, San Diego, Calif.), using the lipofection method described by Felgner et al., *Proc. Natl. Acad. Sci. USA* 84: 7413–7417 (1987). 1 μg of BaculoGold™ virus DNA and 5 μg of the plasmid are mixed in a sterile well of a microtiter plate containing 50 μl of serum-free Grace's medium (Life Technologies Inc., Gaithersburg, Md.). Afterwards 10 μl Lipofectin plus 90 μl Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is rocked back and forth to mix the newly added solution. The plate is then incubated for 5 hours at 27° C. After 5 hours the transfection solution is removed from the plate and 1 ml of Grace's insect medium supplemented with 10% fetal calf serum is added. The plate is put back into an incubator and cultivation is continued at 27° C. for four days.

After four days the supernatant is collected and a plaque assay is performed, as described by Summers and Smith, cited above. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10).

Four days after serial dilution, the virus is added to the cells. After appropriate incubation, blue stained plaques are picked with the tip of an Eppendorf pipette. The agar containing the recombinant viruses is then resuspended in an Eppendorf tube containing 200 μl of Grace's medium. The agar is removed by a brief centrifugation and the supernatant containing the recombinant baculovirus is used to infect Sf9 cells seeded in 35 mm dishes. Four days later the supernatants of these culture dishes are harvested and then they are stored at 4° C. A clone containing properly inserted endokine alpha is identified by DNA analysis including restriction mapping and sequencing of this plasmid.

Sf9 cells are grown in Grace's medium supplemented with 10% heat-inactivated FBS. The cells are infected with the recombinant baculovirus at a multiplicity of infection ("MOI") of about 2 (about 1 to about 3). Six hours later the medium is removed and is replaced with SF900 II medium minus methionine and cysteine (available from Life Technologies Inc., Gaithersburg). 42 hours later, 5 μCi of $^{35}$S-methionine and 5 μCi $^{35}$S-cysteine (available from Amersham) are added. The cells are further incubated for 16 hours and then they are harvested by centrifugation, lysed and the labeled proteins are visualized by SDS-PAGE and autoradiography.

Example 3

Cloning and Expression in CHO Cells

The vector pC4 is used for the expression of endokine alpha protein. Plasmid pC4 is a derivative of the plasmid pSV2-dhfr (ATCC Accession No. 37146). The plasmid contains the mouse DHFR gene under control of the SV40 early promoter. Chinese hamster ovary- or other cells lacking dihydrofolate activity that are transfected with these plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented (see, e.g., Alt, F. W., Kellems, R. M., Bertino, J. R., and Schimke, R. T., 1978, *J. Biol. Chem.* 253:1357–1370, Hamlin, J. L. and Ma, C. 1990, *Biochem. et Biophys. Acta*, 1097:107–143, Page, M. J. and Sydenham, M. A. 1991, *Biotechnology* 9:64–68). Cells grown in increasing concentrations of MTX develop resistance to the drug by overproducing the target enzyme, DHFR, as a result of amplification of the DHFR gene. If a second gene is linked to the DHFR gene, it is usually co-amplified and over-expressed. It is known in the art that this approach may be used to develop cell lines carrying more than 1,000 copies of the amplified gene(s). Subsequently, when the methotrexate is withdrawn, cell lines are obtained which contain the amplified gene integrated into one or more chromosome(s) of the host cell.

Plasmid pC4 contains for expressing the gene of interest the strong promoter of the long terminal repeat (LTR) of the Rous Sarcoma Virus (Cullen et al., *Molec. Cell. Biol.* 5:438–447 (1985)) plus a fragment isolated from the enhancer of the immediate early gene of human cytomegalovirus (CMV) (Boshart et al., *Cell* 41:521–530 (1985)). Downstream of the promoter are BamHI, XbaI, and Asp718 restriction enzyme cleavage sites that allow integration of the genes. Behind these cloning sites the plasmid contains the 3' intron and polyadenylation site of the rat preproinsulin gene. Other high efficiency promoters can also be used for the expression, e.g., the human β-actin promoter, the SV40 early or late promoters or the long terminal repeats from other retroviruses, e.g., HIV and HTLVI. Clontech's Tet-Off and Tet-On gene expression systems and similar systems can be used to express the endokine alpha in a regulated way in mammalian cells (Gossen, M., & Bujard, H. 1992, *Proc. Natl. Acad. Sci. USA* 89: 5547–5551). For the polyadenylation of the mRNA other signals, e.g., from the human growth hormone or globin genes can be used as well. Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC4 is digested with the restriction enzymes BamHI and Asp7 18I and then dephosphorylated using calf intestinal phosphatase by procedures known in the art. The vector is then isolated from a 1% agarose gel.

The DNA sequence encoding the complete endokine alpha protein including its leader sequence is amplified using PCR oligonucleotide primers corresponding to the 5' and 3' sequences of the gene. The 5' primer has the sequence 5' GCG <u>GGA TCC</u> GCC ATC ATG CCT TTA AGC CAT TC 3' (SEQ ID NO:9) containing the underlined BamHI restriction enzyme site followed by an efficient signal for initiation of translation in eukaryotes, as described by Kozak, M., *J. Mol. Biol.* 196:947–950 (1987), and 17 bases of the coding sequence of endokine alpha shown in FIGS. 1A–1B (SEQ ID NO:1). The 3' primer has the sequence 5' GC <u>GGA TCC</u> CTA GGA GAT GAA TTG GGG ATT TG 3' (SEQ ID NO:10) containing the underlined Asp718I restriction site followed by nucleotides complementary to the non-translated region of the endokine alpha gene shown in FIGS. 1A–1B (SEQ ID NO:1).

The amplified fragment is digested with the endonucleases BamHI and Asp718I and then purified again on a 1% agarose gel. The isolated fragment and the dephosphorylated vector are then ligated with T4 DNA ligase. *E. coli* HB 101 or XL-1 Blue cells are then transformed and bacteria are identified that contain the fragment inserted into plasmid pC4 using, for instance, restriction enzyme analysis.

Chinese hamster ovary cells lacking an active DHFR gene are used for transfection. 5 μg of the expression plasmid pC4 is cotransfected with 0.5 μg of the plasmid pSV2-neo using lipofectin (Felgner et al., supra). The plasmid pSV2-neo neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of metothrexate plus 1 mg/ml G418. After about 10–14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1μM, 2μM, 5μM, 10μM, 20μM). The same procedure is repeated until clones are obtained which grow at a concentration of 100–200 μM. Expression of the desired gene product is analyzed, for instance, by SDS-PAGE and Western blot or by reverse phase HPLC analysis.

Example 4

Tissue Distribution of Endokine Alpha Expression

Northern blot analysis was carried out to examine the levels of expression of the gene encoding the endokine alpha protein in human tissues, using methods described by, among others, Sambrook et al., supra. A cDNA probe containing the entire nucleotide sequence of the endokine alpha protein of the present invention (SEQ ID NO:1) was labeled with $^{32}$P using the rediprime™ DNA labeling system (Amersham Life Science), according to manufacturer's instructions. After labelling, the probe was purified using a CHROMA SPIN-100 ™ column (Clontech Laboratories, Inc.), according to manufacturer's protocol number PT1200-1. The purified labelled probe was then used to examine various human tissues for the expression of the gene encoding the endokine alpha protein.

Multiple Tissue Northern (MTN) blots containing various human tissues (H) or human immune system tissues (IM) were obtained from Clontech and were examined with labelled probe using ExpressHyb™ Hybridization Solution (Clontech) according to manufacturer's protocol number PT1190-1. Following hybridization and washing, the blots were mounted and exposed to film at −70° C. overnight, and films developed according to standard procedures.

Expression of the gene encoding an endokine alpha protein of the present invention was detected in human brain striatum and pancreas tissue.

It will be clear that the invention may be practiced otherwise than as particularly described in the foregoing description and examples.

Numerous modifications and variations of the present invention are possible in light of the above teachings and, therefore, are within the scope of the appended claims.

The disclosures of all patents, patent applications, and publications referred to herein are hereby incorporated by reference.

What is claimed is:

1. An isolated protein comprising an amino acid sequence at least 95% identical to amino acids 2 to 169 of SEQ ID NO:2.

2. The protein of claim 1, which comprises an amino acid sequence at least 95% identical to amino acids 1 to 169 of SEQ ID NO:2.

3. The protein of claim 1, which is produced by a recombinant host cell.

4. An isolated protein produced by a method comprising:
   (a) expressing the protein of claim 1 in a cell; and
   (b) recovering said protein.

5. The protein of claim 1, which comprises a heterologous polypeptide.

6. The protein of claim 5, wherein said a heterologous polypeptide comprises the Fc portion of an antibody molecule.

7. A composition comprising the protein of claim 1 and a pharmaceutically acceptable carrier.

8. The protein of claim 1, which is capable of generating or selecting an antibody that specifically binds a polypeptide having an amino acid sequence consisting of SEQ ID NO:2.

9. An isolated protein comprising amino acids 2 to 169 of SEQ ID NO:2.

10. The protein of claim 9, which comprises amino acids 1 to 169 of SEQ ID NO:2.

11. The protein of claim 9, which is produced by a recombinant host cell.

12. An isolated protein produced by a method comprising:
    (a) expressing the protein of claim 9 in a cell; and
    (b) recovering said protein.

13. The protein of claim 9, which comprises a heterologous polypeptide.

14. The protein of claim 13, wherein said a heterologous polypeptide comprises the Fc portion of an antibody molecule.

15. A composition comprising the protein of claim 9 and a pharmaceutically acceptable carrier.

16. An isolated protein comprising an amino acid sequence at least 95% identical to the amino acid sequence encoded by the cDNA in ATCC Deposit No. 97640.

17. The protein of claim 16, which is produced by a recombinant host cell.

18. An isolated protein produced by a method comprising:
    (a) expressing the protein of claim 16 in a cell; and
    (b) recovering said protein.

19. The protein of claim 16, which comprises a heterologous polypeptide.

20. The protein of claim 19, wherein said a heterologous polypeptide comprises the Fc portion of an antibody molecule.

21. A composition comprising the protein of claim 16 and a pharmaceutically acceptable carrier.

22. The protein of claim 16, which is capable of generating or selecting an antibody that specifically binds a polypeptide having an amino acid sequence consisting of SEQ ID NO:2.

23. An isolated protein comprising the amino acid sequence encoded by the cDNA in ATCC Deposit No. 97640.

24. The protein of claim 23, which is produced by a recombinant host cell.

25. An isolated protein produced by a method comprising:
    (a) expressing the protein of claim 23 in a cell; and
    (b) recovering said protein.

26. The protein of claim 23, which comprises a heterologous polypeptide.

27. The protein of claim 26, wherein said a heterologous polypeptide comprises the Fc portion of an antibody molecule.

28. A composition comprising the protein of claim 23 and a pharmaceutically acceptable carrier.

29. An isolated protein comprising 30 contiguous amino acids of SEQ ID NO:2, wherein said protein is capable of generating or selecting an antibody that specifically binds a polypeptide having an amino acid sequence consisting of SEQ ID NO:2.

30. The protein of claim 29, which comprises 50 contiguous amino acids of SEQ ID NO:2.

31. The protein of claim 29, wherein said 30 contiguous amino acids comprise amino acids 44 to 54 of SEQ ID NO:2.

32. The protein of claim 29, which comprises amino acids 44 to 158 of SEQ ID NO:2.

33. The protein of claim 29, wherein said 30 contiguous amino acids comprise amino acids 57 to 68 of SEQ ID NO:2.

34. The protein of claim 29, wherein said 30 contiguous amino acids comprise amino acids 69 to 78 of SEQ ID NO:2.

35. The protein of claim 29, wherein said 30 contiguous amino acids comprise amino acids 94 to 105 of SEQ ID NO:2.

36. The protein of claim 29, wherein said 30 contiguous amino acids comprise amino acids 108 to 132 of SEQ ID NO:2.

37. The protein of claim 29, wherein said 30 contiguous amino acids comprise amino acids 148 to 158 of SEQ ID NO:2.

38. The protein of claim 29, which is produced by a recombinant host cell.

39. An isolated protein produced by a method comprising:
    (a) expressing the protein of claim 29 in a cell; and
    (b) recovering said protein.

40. The protein of claim 29, which comprises a heterologous polypeptide.

41. The protein of claim 40, wherein said a heterologous polypeptide comprises the Fc portion of an antibody molecule.

42. A composition comprising the protein of claim 40 and a pharmaceutically acceptable carrier.

43. An isolated protein comprising 30 contiguous amino acids of the amino acid sequence encoded by the cDNA in ATCC Deposit No. 97640, wherein said protein is capable of generating or selecting an antibody that specifically binds a polypeptide having an amino acid sequence consisting of SEQ ID NO:2.

44. The protein of claim 43, which comprises 50 contiguous amino acids of the amino acid sequence encoded by the cDNA in ATCC Deposit No. 97640.

45. The protein of claim 43, which is produced by a recombinant host cell.

46. An isolated protein produced by a method comprising:
    (a) expressing the protein of claim 43 in a cell; and
    (b) recovering said protein.

47. The protein of claim 43, which comprises a heterologous polypeptide.

48. The protein of claim 47, wherein said a heterologous polypeptide comprises the Fc portion of an antibody molecule.

49. A composition comprising the protein of claim 43 and a pharmaceutically acceptable carrier.

50. An isolated protein comprising an amino acid sequence at least 95% identical to a member selected from the group consisting of:
    (a) amino acids 1 to 17 of SEQ ID NO:2;

(b) amino acids 18 to 43 of SEQ ID NO:2; and (c) amino acids 44 to 169 of SEQ ID NO:2.

51. The protein of claim 50, comprising an amino acid sequence at least 95% identical to amino acids 1 to 17 of SEQ ID NO:2.

52. The protein of claim 50, which is capable of generating or selecting an antibody that specifically binds a polypeptide having an amino acid sequence consisting of SEQ ID NO:2.

53. The protein of claim 51, comprising amino acids 1 to 17 of SEQ ID NO:2.

54. The protein of claim 50, comprising an amino acid sequence at least 95% identical to amino acids 18 to 43 of SEQ ID NO:2.

55. The protein of claim 54, comprising amino acids 18 to 43 of SEQ ID NO:2.

56. The protein of claim 50, comprising an amino acid sequence at least 95% identical to amino acids 44 to 169 of SEQ ID NO:2.

57. The protein of claim 56, comprising amino acids 44 to 169 of SEQ ID NO:2.

58. The protein of claim 50, which is produced by a recombinant host cell.

59. An isolated protein produced by a method comprising:

(a) expressing the protein of claim 50 in a cell; and (b) recovering said protein.

60. The protein of claim 50, which comprises a heterologous polypeptide.

61. The protein of claim 60, wherein said a heterologous polypeptide comprises the Fc portion of an antibody molecule.

62. A composition comprising the protein of claim 50 and a pharmaceutically acceptable carrier.

* * * * *